(12) United States Patent
Markus et al.

(10) Patent No.: US 9,717,240 B2
(45) Date of Patent: *Aug. 1, 2017

(54) APPLICATIONS OF MICROENCAPSULATED ESSENTIAL OILS

(71) Applicant: BotanoCap Ltd., Ashkelon (IL)

(72) Inventors: Arie Markus, Beer Sheva (IL); Pnina Strongin, Beer-Sheva (IL); Charles Linder, Rehovot (IL)

(73) Assignee: BOTANOCAP LTD., Ashkelon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/933,594

(22) Filed: Nov. 5, 2015

(65) Prior Publication Data

US 2016/0050914 A1 Feb. 25, 2016

Related U.S. Application Data

(60) Continuation of application No. 14/272,098, filed on May 7, 2014, now Pat. No. 9,210,926, which is a division of application No. 12/222,741, filed on Aug. 14, 2008, now Pat. No. 8,753,676, and a continuation-in-part of application No. PCT/IL2007/000213, filed on Feb. 15, 2007.

(60) Provisional application No. 61/087,755, filed on Aug. 11, 2008, provisional application No. 60/873,939, filed on Dec. 11, 2006, provisional application No. 60/773,313, filed on Feb. 15, 2006.

(51) Int. Cl.

| | |
|---|---|
| *A01N 25/28* | (2006.01) |
| *A01N 65/00* | (2009.01) |
| *A01N 65/12* | (2009.01) |
| *A01N 65/22* | (2009.01) |
| *A23L 3/3463* | (2006.01) |
| *A23L 3/3472* | (2006.01) |
| *A61K 9/50* | (2006.01) |
| *A61K 35/60* | (2006.01) |
| *A61K 36/13* | (2006.01) |
| *A61K 36/53* | (2006.01) |
| *A61K 47/12* | (2006.01) |
| *C11D 3/50* | (2006.01) |
| *A01N 65/28* | (2009.01) |
| *A01N 65/06* | (2009.01) |
| *A01N 65/08* | (2009.01) |
| *A23P 10/30* | (2016.01) |
| *A23L 33/105* | (2016.01) |
| *A23L 33/135* | (2016.01) |

(52) U.S. Cl.
CPC ............ *A01N 25/28* (2013.01); *A01N 65/00* (2013.01); *A01N 65/06* (2013.01); *A01N 65/08* (2013.01); *A01N 65/12* (2013.01); *A01N 65/22* (2013.01); *A01N 65/28* (2013.01); *A23L 3/3463* (2013.01); *A23L 3/3472* (2013.01); *A23L 33/105* (2016.08); *A23L 33/135* (2016.08); *A23P 10/30* (2016.08); *A61K 9/5015* (2013.01); *A61K 9/5031* (2013.01); *A61K 35/60* (2013.01); *A61K 36/13* (2013.01); *A61K 36/53* (2013.01); *A61K 47/12* (2013.01); *C11D 3/505* (2013.01); *A23V 2002/00* (2013.01)

(58) Field of Classification Search
CPC ..................................................... A01N 25/28
See application file for complete search history.

(56) References Cited

U.S. PATENT DOCUMENTS

| | | |
|---|---|---|
| 4,547,360 A | 10/1985 | Perlberg |
| 4,548,764 A | 10/1985 | Munteanu et al. |
| 5,069,231 A | 12/1991 | Rutherford |
| 5,576,009 A | 11/1996 | Nastke et al. |
| 5,925,464 A | 7/1999 | Mulqueen et al. |
| 6,106,838 A | 8/2000 | Nitsas |
| 6,506,397 B1 | 1/2003 | Thies |
| 6,649,660 B2 | 11/2003 | Ninkov |
| 6,921,539 B2 | 7/2005 | Ninkov |
| 8,753,676 B2 * | 6/2014 | Kritzman ............... A01N 65/00 424/408 |
| 2004/0052865 A1 | 3/2004 | Gower et al. |
| 2006/0165746 A1 | 7/2006 | Markus et al. |

FOREIGN PATENT DOCUMENTS

| | | |
|---|---|---|
| CN | 1561792 A | 1/2005 |
| EP | 0252897 A2 | 1/1988 |
| WO | 9413139 A1 | 6/1994 |
| WO | 02068335 A2 | 9/2002 |
| WO | 2004/034791 A1 | 4/2004 |
| WO | 2004098767 A1 | 11/2004 |

* cited by examiner

*Primary Examiner* — Rosanne Kosson

(74) *Attorney, Agent, or Firm* — Vorys, Sater, Seymour & Pease LLP

(57) ABSTRACT

Method for the preparation of microencapsulated essential oils or a formulation thereof for various non-agricultural applications.

17 Claims, No Drawings

APPLICATIONS OF MICROENCAPSULATED ESSENTIAL OILS

FIELD OF THE INVENTION

This invention relates to microencapsulated essential oil formulations suitable for non-agricultural applications. The present application also relates to microcapsules of essential oils having a solid core, processes for the preparation thereof and their application as preservative and disinfectant and insect repellant products for the storage of agricultural products and foods.

BACKGROUND OF THE INVENTION

Recently, several studies have focused on the potential use of essential oils in biological control of microorganisms and different insect pests. The essential oils may be more rapidly degraded in the environment than synthetic compounds, and some have increased specificity that favors beneficial insects. Their action against stored product insects has been extensively studied. Despite most promising properties, problems related to essential oil volatility, poor water solubility, and aptitude for oxidation have presented a real problem that made essential oil formulations difficult to use as control systems and eventually apply to the target environment.

SUMMARY OF THE INVENTION

It has now been surprisingly found that certain formulations containing a single or a combination of microencapsulated essential oils may be used for a variety of non-agricultural purposes, particularly for the treatment or prevention of certain ailments of or damages to the target.

A person skilled in the art would realize that for a formulation to be successful in achieving the desired effect a great extent of experimental work may be needed. While a certain type of microencapsulation method may provide a microcapsule formulation which is beneficial for a certain application, it may nevertheless be ineffective in another application. Similarly, while a certain essential oil may be known to have a certain activity, for example, antimicrobial activity, its efficiency in every antimicrobial application cannot be assured. As the artisan would realize, these differences may arise from a variety of factors, such as release rates from the microcapsules, degrees of permeability, concentration, efficiency in slow release and small amounts, distribution of the microcapsules on the target, deactivating effect of the microcapsule shell, presence of other additives or adjuvants in the microcapsule or carrier containing thereof, conditions at the target prior to or after application of the essential oil formulation, shelf-life, the presence of various additives, etc.

The present application discloses numerous aspects of microencapsulation of essential oils, as follows:

The Formulations

In this first aspect of the present invention, there is provided a method (herein referred to as the "method of the invention") for the preparation of a suspension of microcapsules, each comprising at least one essential oil, said method comprising:

(a) admixing at least one alkanoic acid with at least one essential oil;

(b) admixing the mixture of step (a) with an aqueous basic solution to obtain a suspension; and (c) admixing into the suspension of step (b) an aqueous salt solution comprising at least one multivalent cation, thereby obtaining a suspension of microcapsules comprising said at least one essential oil.

In one embodiment, step (a) is carried out without necessitating any solvent.

In another embodiment, the at least one alkanoic acid is first dissolved or suspended in a solvent, being preferably a water-immiscible liquid.

In one embodiment, said water-immiscible liquid is an essential oil.

In another, it is not an essential oil. Where the water-immiscible liquid is not an essential oil, it may be selected amongst water-insoluble organic solvents which are not reactive under the conditions employed in the method. Non-limiting examples of such water-immiscible liquids are alkanes (such as hexane and petroleum ether), ethers (such as diethyl ether, butyl ethyl ether), alcohols, and ketones.

In another embodiment, the solid alkanoic acid is melted before being added to the essential oil or water-immiscible carrier. In a preferred embodiment, the water-immiscible liquid is an edible water-immiscible liquid.

The aqueous basic solution used in step (b) may be a solution of a single monovalent base such as NaOH or a mixture of two or more such bases, e.g., NaOH and KOH, or NaOH and $Na_2CO_3$. In one embodiment, the base is an inorganic base. In another embodiment, the base is an organic base. In another embodiment, the base is an organic base. In a preferred embodiment, the aqueous basic solution is an edible aqueous basic solution.

In a preferred embodiment, the monovalent base is a base of sodium or potassium.

In another embodiment, the suspension obtained in step (b) is a dispersion of micelles. In another embodiment, the suspension obtained in step (b) is a clear suspension.

The salt solution of multivalent cations added in step (c) of the method of the invention is a solution of inorganic metal salts containing cations having a charge greater than +1. In one embodiment, the inorganic metal cations are those of Group II of the periodic table. Non-limiting examples of such cations are the multivalent cations of Ca, Mg, Fe, and Al. Preferably, the multivalent cation is Ca.

It should be understood that where a certain atom has a multiple number of cations of different charges, all such cations fall within the scope of the present invention.

In one embodiment, the multivalent cation is different from Ca.

In another embodiment, the multivalent cation is different from Mg.

In another embodiment, the multivalent cation is different from Fe.

In another embodiment, the multivalent cation is different from Al.

In another embodiment, the multivalent cation is different from any one of Ca, Mg, Fe, or Al.

In another embodiment, the aqueous salt solution of step (c) comprises a mixture of two or more multivalent salts. Such mixtures may be of salts having different cations, e.g., $CaCl_2$ and $MgCl_2$, mixtures of salts having different counter anion, e.g., $CaCl_2$ and $Ca(OH)_2$, or mixtures of salts having cations of different charge, e.g., $CaCl_2$ and $FeCl_3$. In a preferred embodiment, the aqueous salt solution is an edible aqueous salt solution.

The salt solution of multivalent cations may alternatively be of organic molecular ions having a positive charge greater than +1, as disclosed above. Non-limiting examples of multivalent organic cations are ammonium salts of di- or trior tetraamines, quarternized polyamines and others. As with the inorganic metal salt solution, the organic salt solution may also comprise two or more different organic salts.

The multivalent salts may be added to the reaction mixture neat or as an aqueous solution, e.g., of metal salts such as $Ca(OH)_2$, $CaCl_2$, $MgCl_2$ or $FeSO_4$.

The at least one "alkanoic acid" is an organic carboxylic acid of the general formula R—COOH, wherein R is an aliphatic carbon chain which may be either saturated and/or unsaturated and the —COOH is the carboxylic acid group as known in organic chemistry. Within the scope of the present invention, the terms alkanoic acid and fatty acid are used interchangeably.

In one embodiment, the alkanoic acid is a water-immiscble compound. Typically, the R group is an aliphatic chain having a backbone of between 10 and 45 carbon atoms. The backbone may be substituted or unsubstituted. In a preferred embodiment, such optional substitution does not have an effect on the hydrophobicity of the carbon chain. In a preferred embodiment, the alkanoic acid is an edible alkanoic acid.

In one embodiment of the invention, said alkanoic acid is selected amongst alkanoic acids having melting point temperatures higher than 25° C.

Non-limiting examples of saturated alkanoic acids which may be encapsulated by the method of the invention are decanoic acid, dodecanoic acid, tetradecanoic acid, hexadecanoic acid, octadecanoic acid, eicosanoic acid, docosanoic acid, and tetracosanoic acid.

Non-limiting examples of unsaturated alkanoic acids are 11-octadecenoic acid, 5,8,11,14-eicosatetraenoic acid, omega-3 fatty acid and others.

Non-limiting examples of omega-3 fatty acids include α-linolenic acid (18:3-omega-3), octadecatetraenoic acid (18:4-omega-3), eicosapentaenoic acid (20:5-omega-3) (EPA), docosahexaenoic acid (22:6-omega-3) (DHA), docosapentaenoic acid (22:5-omega-3) (DPA), eicosatetraenoic acid (20:4-omega-3), uncosapentaenoic acid (21:5-omega-3), docosapentaenoic acid (22:5-omega-3) including any derivative thereof.

In one embodiment, the omega-3 fatty acid is a mixture of two or more such fatty acids.

Possible derivatives of omega-3 fatty acids may include ester derivatives, branched or unbranched $C_1$-$C_{30}$ alkyl esters, branched or unbranched $C_2$-$C_{30}$ alkenyl esters, or branched or unbranched $C_3$-$C_{30}$ cycloalkyl esters such as phytosterol esters.

In one embodiment, said fatty acids are obtained by extraction from natural sources including, without being limited to, aquatic organisms such as anchovies, capelin, Atlantic cod, Atlantic herring, Atlantic mackerel, Atlantic menhaden, salmonids, sardines, shark, and tuna; plants such as flax, and vegetables; and microorganisms such as fungi and algae.

The term "essential oils" encompasses within the scope of the present invention also botanical oils and lipids.

Non-limiting examples of essential oils are sesame oil, pyrethrum, glycerol-derived lipids or glycerol fatty acid derivatives, cinnamon oil, cedar oil, clove oil, geranium oil, lemongrass oil, *angelica* oil, mint oil, turmeric oil, wintergreen oil, rosemary oil, anise oil, cardamom oil, caraway oil, chamomile oil, coriander oil, guaiacwood oil, cumin oil, dill oil, mint oil, parsley oil, basil oil, camphor oil, *cananga* oil, citronella oil, *eucalyptus* oil, fennel oil, ginger oil, copaiba balsam oil, *perilla* oil, cedarwood oil, jasmine oil, palmarosa sofia oil, western mint oil, star anis oil, tuberose oil, neroli oil, tolu balsam oil, patchouli oil, palmarosa oil, *Chamaecyparis obtusa* oil, Hiba oil, sandalwood oil, petitgrain oil, bay oil, vetivert oil, bergamot oil, Peru balsam oil, bois de rose oil, grapefruit oil, lemon oil, mandarin oil, orange oil, oregano oil, lavender oil, *Lindera* oil, pine needle oil, pepper oil, rose oil, iris oil, sweet orange oil, tangerine oil, tea tree oil, tea seed oil, thyme oil, thymol oil, garlic oil, peppermint oil, onion oil, linaloe oil, Japanese mint oil, spearmint oil and others as disclosed herein throughout.

In one embodiment, the essential oils are volatile oils.

Thus the invention also claims the encapsulation of a solid porous core impregnated with essential oils comprising primarily or in part volatile components encapsulated in microcapsules made by the interfacial polymerization of isocyanates to form encapsulating shells of polyurethanes, polyureas or combinations of polyurethanes and polyureas.

In another embodiment, the essential oils are spice plant essential oils.

In another embodiment, the essential oil is selected amongst citronella oil, geranium oil, tea tree oil, lavender oil, clove pine oil, *eucalyptus* oil, thyme oil, and oregano oil.

As the person skilled in the art would recognize, the specific essential oil or a combination of essential oils will be selected based on the specific application.

In one embodiment, the microencapsulated essential oil microcapsules obtained from the method of the invention are waxy or solid particles.

In another embodiment, the microcapsules are not separated from the medium and the formulation is used as is.

In yet another embodiment, the above method further comprises the step of filtering and collecting the microencapsulated essential oil microcapsules. When separating the solid microcapsules from the aqueous media, small amounts of essential oils may remain unencapsulated. In order to obtain oil-dry microcapsules, an absorbent capable of absorbing the excess oil is added, typically in small amounts. The absorbent may be selected amongst, for example, Celluloses, starch powders or Aerosil™ silicas such Aerosil™ 200 or 300, commercially available from Degussa, clays, zeolites, atapulgite, and other inorganic minerals. In some applications the Aerosil™ is the preferred absorbent.

In another embodiment, the method of the invention may further comprise the step of adding at least one surfactant. The surfactant may be ionic or non-ionic and may be added to the solution or suspension neat or in solution, e.g., water solution, during the manufacturing of the microcapsules in order to facilitate or control the size of the microcapsules, or after the microcapsules have been formed in order to break up a gel that results from the microencapsulation and afford a flowable formulation. One especially preferred surfactant is sodium dodecyl sulfate (SDS). Preferably the surfactant is added in concentrations of 0.1 to 10%, and most preferably in concentrations of 0.5% to 5% of the total weight of the formulation.

In another embodiment, the method further comprises the addition of at least one additive, preferably added before step (c). The at least one additive may be a solid, a liquid, a solution, a suspension, or a mixture of two or more such additives.

Non-limiting examples of classes of additives which may be used are active pharmaceutical agents, natural or synthetic antioxidants, food supplements, vitamins, colorants, odorants, oils, fats, flavors, nonvolatile natural essential oils or other dispersants or emulsifiers.

Non-limiting examples of specific additives which may be used are gamma-linolenic acids, citrus oils such as orange oil, nutritional supplements such as Vitamin A, Vitamin E, Vitamin C, and Vitamin D, tocopherols, tocotrienols, phytosterols, Vitamin K, beta-carotene, marine oils, omega-3 fatty acids, $CoQ_{10}$, lipid soluble derivatives of polar antioxidants, such as ascobyl fatty acid esters, plant extracts such as rosemary, sage and oregano oils, algal extracts, and synthetic antioxidants such as BHT, TBHQ, ethoxyquin, alkyl gallates and hydroquinones or natural antioxidants.

Other non-limiting examples of preferred additives in addition to surfactants are steric barrier polymers, which help maintain particle separation. These steric barrier polymers may be selected, without limitation, from polyvinylpyrrolidone (PVP), polyvinyl alcohol (PVA) and poly (ethoxy)nonylphenol. In cases where it is necessary to adjust the pH of the finished microcapsule formulation as, for example, when the microcapsule suspension is combined with other pesticides, conventional reagents for adjustment of acidity or alkalinity may be used. Such agents may for example include hydrochloric acid, citric acid, sodium hydroxide, sodium carbonate, and sodium bicarbonate.

Once prepared, the liquid or solid formulation may be preserved until it is used. Often it is most convenient to bottle or can the suspension containing the encapsulated essential oil, in which case it may be desirable to add formulation adjuvants before storing to improve suspension stability and ease of application. These adjuvants may be selected amongst density balancing agents, surfactants, thickeners, biocides, dispersants, antifreeze agents, salts, and the like. Typically, the adjuvant is be added at a concentration of from about 0.01% to about 30% by weight.

The present invention also provides a microencapsulated essential oil formulation comprising a plurality of microcapsules, each containing at least one essential oil, wherein said formulation or microencapsulated essential oil is prepared according to the method of the invention.

Within the scope of the present invention, the term "formulation" refers to a combination of the microcapsules prepared according to the method of the present invention, or employed by any one application of the present invention and any other agent which may be the media to which the microcapsules are added. The formulation according to the invention may also comprise any additive as disclosed. The term refers also to the suspension or dispersion of the microcapsules in the media (e.g., solid or liquid).

The formulations of the invention may generally be prepared according to known methods in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Generally speaking, where the formulations are intended as pharmaceutical formulations, pharmaceutically acceptable carriers such as vehicles, adjuvants, excipients, or diluents may be required. Such pharmaceutically acceptable carriers are well-known to those who are skilled in the art and are readily available to the public. It is preferred that the pharmaceutically acceptable carrier be one which is chemically inert to the essential oils or to any of the other compounds contained within or on the surface of the microcapsules. The choice of a pharmaceutically acceptable carrier may be determined in part by the particular essential oil, as well as by the particular method used to administer the formulation to the subject (animal or human).

The formulations of the invention which are suitable for human or animal use, e.g., repellant, antimicrobial, food additive, are preferably suitable for oral administration or topical administration onto the skin of the subject. Such formulation can therefore consist of (a) liquid suspensions, such as an effective amount of the essential oil microcapsules suspended in carriers, such as water, saline, or orange juice; (b) capsules, sachets, tablets, lozenges, and troches, each containing a predetermined amount of the active ingredient, as solids or granules; (c) powders; and (d) suitable emulsions.

Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent.

Capsule forms can be of the ordinary hard- or soft-shelled gelatin type containing, for example, surfactants, lubricants, and inert fillers, such as lactose, sucrose, calcium phosphate, and corn starch.

Tablet forms can include one or more of lactose, sucrose, mannitol, corn starch, potato starch, alginic acid, microcrystalline cellulose, acacia, gelatin, guar gum, colloidal silicon dioxide, croscarmellose sodiumk talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers.

In another aspect of the invention, there is provided a microcapsule prepared according to the method comprising:

(a) admixing at least one alkanoic acid with at least one essential oil;

(b) admixing the mixture of step (a) with an aqueous basic solution to obtain a suspension;

(c) admixing into the suspension of step (b) an aqueous salt solution comprising at least one multivalent cation; and (d) collecting the microcapsules from the aqueous media, thereby obtaining a plurality of microcapsules of at least one microencapsulated essential oil.

In one embodiment, the microcapsule prepared has an amphiphatic shell which substantially surrounds a core containing at least one essential oil.

The core may be a liquid core or a solid care.

When the core is a solid core, the obtained microcapsules are particularly useful in reducing bacterial, fungal and insect infestations. In particular the micro encapsulated essential oils comprise a solid porous core which contains within the pores and on the surface an essential oil or mixture of essential oil and may also contain additives such as synthetic disinfectant or preservative or insecticides or pesticides or insect growth regulators all of which are encapsulated by a thin polymeric film formed around the impregnated particulate core.

The solid core may be any porous inorganic or organic material with dimensions on 0.1 to 500 microns. Preferably 1 to 100 microns in diameter. It is preferred that this solid core be highly porous in order to absorb a large amount of material. In one case it is an inorganic material such as the Aerosils.

Thus, in one preferred approach the solid core matter appears as micron sized particles and is placed in a rotating drum and the essential oil with the reactive monomer is then sprayed into the drum and left for the time it takes to absorb into the porous particles. Subsequently an aqueous solution, as a spray, is applied to the inside of the rotating drum which said spray contains the monomers that react with the monomers in the essential oils to form the encapsulating film around the solid core that contains the essential oils and other components. In another case a second coating a polymer or a wax may be applied by a non aqueous solution of the polymer or wax.

In a preferred case the essential oil contains di or polyisocyante such as toluene diisocyanate (TDI) or 4,4" diphenyl diisocyanate (polyisocyante) and the aqueous solution contains polyhydroxy compounds which forms polyurethanes with the isocyanates and/or amines which react with said di- or polyisocyante to form poly ureas. The resulting powder obtained after the manufacturing process may then be further formulated with other additives or may be used as is.

In another embodiment, the amphiphatic shell is the multivalent alkanoate derived from at least one alkanoic acid and a multivalent cation.

As known to a person skilled in the art, an amphiphile is a molecule having both hydrophobic and hydrophilic groups. The alkanoic acids employed in the method of the invention, are amphiphiles. In the alkanoic acids of the general formula RCOOH, as defined above, R is the aliphatic chain having hydrophobic properties with the group —COOH or a salt form thereof having hydrophilic properties. Without wishing to be bound by theory, the amphiphatic shell is constructed with the hydrophobic groups embedded in the essential oil core and the hydrophilic groups being exterior thereto, pointing outwards on the surface of the microcapsules.

Further provided is a microcapsule having an amphiphatic shell surrounding a core comprising at least one essential oil, wherein said amphiphatic shell is a multivalent salt form of at least one alkanoic acid.

This mixture, which is absorbed within the solid core, may also contain dissolved therein other components such as synthetic preservatives or disinfectants and may also contain additives such as synthetic disinfectant or preservative or insecticides or pesticides or insect growth regulators which are absorbed into the pores and on the surface of the porous support. This combination of the solid core and the essential/monomer is then exposed to an aqueous mist or spray or solution which contains the monomers that react with the monomers in the essentials oils to form the encapsulating film around the solid core that contains the essential oils and other components. A subsequent coating which may be a polymer or a wax may be applied by a non aqueous solution of the polymer or wax.

According to a preferred embodiment, there is provided a method for repelling, exterminating or managing an insect population wherein this formulation is prepared in an interfacial polymerization process by:

(I) dissolving a diisocyanate or a polyisocyanate within a cold mixture of said essential oils, optionally further dissolving at least one additive in said cold mixture;

(II) absorbing the essential oil solution obtained in steps (I) on microporous particles and then exposing these said particles with the absorbed essential oil solutions to cold aqueous mist or spray or solution containing diamines or polyamines and/or polyalcohols, thereby encapsulating said essential oils and said additives in a solid microencapsulated core.

Preferably, said diamine or polyamine that form polyureas with the isocyanates are selected from the group consisting of ethylenediamine, diethylenetriamine, propylenediamine Tetraethylenepentaamine, pentamethylene hexamine, alpha, omega-diamines, propylene-1,3-diamine, tetramethylenediamine, pentamethylenediamine and 1,6-hexamethylenediamine polyethyleneamines, diethylenetriamine, triethylenetriamine, pentaethylenehexamine, 1,3-phenylenediamine, 2,4-toluoylenediamine, 4,4'-diaminodiphenylmethane, 1,5-diaminoaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole, bis(hexamethylentriamine) and 1,4,5,8-tetraminoanthraquinone.

Preferably, said di- or polyalcohol is selected from the group consisting of polyhydric alcohols, such as ethylene glycol, diethylene glycol, propylene glycol, 1,4-butane diol, 1,4 hexane diol, dipropylene glycol, cyclohexyl 1,4 dimethanol, 1,8 octane diol and polyols such as poly(ethylene glycols), poly(propylene glycols), poly(tetramethylene glycols) with average molecular weights in the range of 200-2000, trimethylolpropane, glycerol, hexane, triols and pentaerythrytol, 1,3-phenylenedihydroxy, 2,4-toluoylenedihydroxy, 4,4'-dihydroxydiphenylmethane, 1,5-dihydroxyoaphthalene, 1,3,5-trihydroxybenzene, 2,4,6-trihydroxytoluene, 1,3,6-trihydroxynaphthalene, 2,4,4'-trihydroxydiphenyl ether and hydrolyzed polyvinyl alcohols.

In another method of forming the encapsulating membrane the encapsulating membrane is formed between an alkanoic acid dissolved in the essential oil which is absorbed onto or into the solid particle which will form the core and then this alkanoic acid will react with a basic solution of a salt of a multivalent cations having a charge greater than +1. such as inorganic metal cations are those of Group II of the periodic table (e.g., the multivalent cations of Ca, Mg, Fe, and Al) that forms the encapsulating membrane around the solid core by a process of complexation. In this approach an alkanoic acid is added to the essential oil and both are adsorbed onto and into the particle that will form the core of the microcapsule. This is then exposed to a mist or spray or solution, which in one preferred case is an aqueous solution containing comprising at least one multivalent cation. The multivalent cations react with the alkanoic acid to form a complex which forms the encapsulating membrane around the solid core.

Therefore, according to a preferred embodiment, there is provided a method for the preparation of a microencapsulated essential oil formulation being in a solid form, whereas this formulation comprises a dispersion of microcapsules in a nonvolatile solid vehicle, such that each microcapsule comprises at least one essential oil, this method comprising:

(a) admixing at least one alkanoic acid and at least one essential oil with at least one absorbent thereby obtaining a solid mixture;

(b) optionally admixing at least one additive with said absorbent and said solid mixture;

(c) exposing the solid mixture of any of steps (a) or (b) to an aqueous solution comprising at least one multivalent cation, thereby obtaining a microencapsulated essential oil formulation, being in a solid form whereas said formulation comprises a dispersion of microcapsules in a nonvolatile solid vehicle, such that each microcapsule comprises at least one essential oil.

In one embodiment, the essential oil and reactants that form the encapsulating membrane (isocyanate reagents, or alkanoic acids) and additives may be added to the solid core in a water-immiscible liquid.

The microcapsules disclosed and/or a formulation containing them may be used in a great variety of applications.

In one embodiment, the formulation is a pharmaceutical formulation for use by human subjects as well as by non-human subjects. The pharmaceutical formulation may be used for example as an antimicrobial formulation.

In another embodiment, the formulation is a non-pharmaceutical antimicrobial formulation.

In still another embodiment, the formulation is an antiseptic formulation.

In yet another embodiment, the formulation is a repellent or an insecticidal formulation for use, for example, in the repelling or extermination of household or environmental insects.

In another embodiment, the formulation is used for the delivery of food additives into foods and beverages consumed by humans and/or animals. Thus, preferably, all of the ingredients are edible, thereby forming an edible microencapsulated essential oil formulation.

The present invention also provides a kit or a commercial package comprising the formulation of the invention. The kit may be a one-component kit or a two-component kit comprising a first container contained therein a suspension of at least one microcapsule encapsulating volatile essential oil and a second container contained therein a non-volatile vehicle. Optionally, the kits of the present invention may also comprise instructions how to apply the two components to the target environment as to achieve the desirable effect.

The kit formulation or single component formulations may be presented in a solid or a liquid form and in concentrated or diluted state and may be applied to the target by, for example, hand, a sponge or a piece of cloth, which was pre absorbed by the formulation, or by hand-held spray.

When used as a powder it may be distributed to the surfaces of containers or confined area or it may be packaged in porous bags or bottles and placed strategically in containers or confined areas containing fruits, vegetables and grains for the purpose of disinfection and preservatives against microbial or fungal growth for example or insect infestation. The porous packages or containers may be flexible or rigid, and they may be constructed of paper plastics or metals or as a combination of different materials.

Each of the applications disclosed hereinnext may utilize the same or different microcapsule formulation. The choice of a formulation is determined by several factors, such as the physical, chemical, and/or the biological properties of the essential oil or essential oil combination; the mode of application; and the properties of the target to which the formulation is to be applied.

Generally, the formulations used in the present invention comprise at least one encapsulated essential oil. A formulation may be the novel formulation disclosed hereinabove or microcapsule formulations prepared by interfacial polymerization, as will be detailed below. Without being limited by the classification used herein, the formulations employed in each of the applications of the present invention may be classified as follows:

1. Homogeneous formulation—a formulation of the same microcapsules, containing the same essential oil or the same mixture of essential oils;

2. Heterogeneous formulation—a formulation which comprises at least two different types of microcapsules, each type containing different essential oils or different mixtures of essential oils. The number of different essential oils or mixtures thereof may vary depending on the application.

In one embodiment, the heterogeneous formulation comprises two types of microcapsules, a first type containing a first essential oil or a first mixture of essential oils, and a second type containing a second essential oil or a second mixture of essential oils, wherein said first essential oil or first mixture of essential oils is different from said second essential oil or from said second mixture of essential oils, respectively. The ratio between the two types of microcapsules, namely between the first and second essential oil or the first and second mixture of essential oils, may vary and may, for example, be 1:1, 1:2, 1:5, 1:10, 1:100, 2:1, 5:1, 10:1, 100:1, respectively, etc.

A first heterogeneous formulation may comprise microcapsules that contain only *eucalyptus* oil along with microcapsules that contain only oregano oil at a ratio of 1:1. A second formulation may comprise microcapsules that contain tea tree oil along with microcapsules that contain each a mixture of oregano oil and *eucalyptus* oil, wherein the ratio between the microcapsules containing tea tree oil and microcapsules containing the mixture is 1:2, and the ratio of the oregano oil and the *eucalyptus* oil in said mixture is 1:1.

Additionally, the heterogeneous formulations may for example comprise microcapsules that contain essential oils together with microcapsules that contain non-essential oil agents.

In another embodiment, said heterogeneous formulation comprises at least two types of microcapsules, one containing an essential oil and the other containing an additive as herein defined.

In another embodiment, the formulation comprises two different microcapsules, the first containing an essential oil and the second containing a mixture of essential oil and an additive.

In yet another embodiment, the formulation comprises at least two types of microcapsules, each type being prepared by a different method, e.g., one prepared by interfacial polymerization and the other by the method of the invention.

In still another embodiment, the formulation comprises at least two types of microcapsules each prepared by interfacial polymerization using a different polymeric chain. For example, one type of microcapsule shell is a polyurethane shell and another type has a polyurea shell.

3. Barrier forming formulation—refers to a formulation which is capable of forming a physical barrier after having been applied to the target and dried and at the same time capable of exerting a desired effect, e.g., repellent effect, insecticide, herbicide, fungicide, bactericide, etc.

A barrier forming formulation is adapted based on its target application to form barriers or films of various thicknesses, permeability, porosity, water solubility, heat stability, and other physical parameters that may determine the rate of release of essential oils therefrom.

In certain embodiments, the physical barrier or film formed has an effect on the release rate of the essential oil from the microcapsules, or from the combined coating of the microcapsules and polymer film such that after the essential oil is released from the microcapsules its rate of evaporation is further reduced by the polymer coating.

In other embodiments, the physical barrier formed has no effect on the release rate and is used as a mere barrier to the crossing of various microorganisms and/or contaminants (physical, biological or chemical). In such embodiments the combination of the essential oil activity and the barrier properties of the coating polymer may have an additive or synergistic effect on the ensued results.

In some other embodiments, the microcapsules comprise volatile essential oils, and a vehicle which is typically chosen from a variety of low-volatile or non-volatile essential oils that are liquids or solids at room temperature.

In another embodiment, the vehicle is not an essential oil.

Without wishing to be bound by theory, when a formulation of encapsulated essential oil is applied onto the target it dries and begins exerting its effect upon contact. The initial effect is exerted by the vehicle (carrier), which although optionally being high boiling in nature, is responsible for the initial effect. As soon as the essential oil begins discharging from the microcapsules, the additive or synergistic effect of both the encapsulated and non-encapsulated essential oils (or non-essential oil vehicle) is observed.

While the distinction between homogenous and heterogeneous formulations is made on the basis of the content of the microcapsules and not the vehicle, the film forming formulations may depend to some extent on the nature of the vehicle. As stated hereinbefore, the film forming formulations allow the formation of a physical barrier or a film which engulfs the treated object, thus preventing or reducing permeation of various microorganisms and pathogens or escape of water and other chemicals from the target (for example in case of post-harvest fruits and vegetables, as will be disclosed herein below). The formation of the barrier may occur by applying, e.g. spraying, it onto the target at a concentration which upon evaporation of the liquid media (e.g. the water in which the microcapsules were prepared, not the vehicle) results in a layer of solid material which is preferably in the shape of a condensed film. The thickness of the film will depend on the concentration of the formulation, the size of the microcapsules, the vehicle (solid or liquid), the number of applications onto the same site or object, the method of application and the degree of dryness.

The film may also be formed by an initial application of a formulation of the invention which in addition to the encapsulated essential oil and the vehicle also includes an agent capable of complexing and/or polymerizing on contact with an agent which is applied thereafter. For example, the formulation of the invention may contain or be treated with a fatty acid such as lauric acid before being applied onto the target surface. After application of the formulation, an aqueous solution of a complexing agent such as calcium chloride may be applied on the site of first application, thereby allowing formation of a film in which the microcapsules are embedded.

As used herein, the expression "encapsulated essential oil", "encapsulation" or any lingual variation thereof refers to a granule of any shape and size, which is capable of holding therein one or more essential oils.

One example of such encapsulation is microencapsulation. The preferred microcapsule is one having from 10 to 98%, or more preferably from 60-95% of its weight an essential oil and which is prepared, in one preferred embodiment, by the method of the invention.

In another embodiment, the microcapsules employed along with or in place of the microcapsules of the invention are microcapsules obtained by interfacial polymerization of isocyanate. Such polymerization affords a microencapsulating shell of polyurethanes, polyureas or combinations thereof, as disclosed for example in WO 04/098767. Such a microcapsule typically has an average size of between 0.1 and 100 microns. Other suitable microcapsules may be prepared by such methods as disclosed for example in WO 94/13139, EP0252897, U.S. Pat. No. 5,576,009 and U.S. Pat. No. 5,925,464.

The encapsulated essential oil formulations may comprise a variety of microcapsules not only in term of their content but also in terms of the methods of their preparations. Thus, the formulations may comprise microcapsules of a variety of sizes, shapes, chemical and physical parameters.

The term "non-volatile vehicle" as used herein refers generally to an organic agent that remains with the microcapsule on the treated object after application and which preferably exerts an additive or synergistic effect. Such a vehicle may be a liquid or a solid (pure or mixture) having a high boiling or melting point and which rate of evaporation from the target, after application thereto, is smaller as compared to that of the encapsulated essential oil. Such vehicles or carriers may for example be non-volatile essential oils, non-volatile botanical oils, non-volatile or solid terpenes, and lipids.

Generally, the vehicle is never water alone. However, in various embodiments it may be necessary to use water as the major component of the formulation. In such exemplary cases when the microcapsules are made in aqueous solutions, or when water is added to allow better fluidity and sprayabillity or when the formulation is packaged or stored in water, the non-volatile vehicle may be added to the water solution which acts as a medium and has no beneficial effect on such as the repelling, insecticidal, pesticidal, larvicidal or ovicidal characteristics of the formulation.

The liquid essential oil and lipid vehicle are preferably those having boiling points higher then 250° C., preferably higher then 300° C. Such high boiling point essential oils may for example be Pyrethrins. An example of a lipid is sesame oil or cottonseed oil.

The term "solid vehicle" refers to a solid agent, in a pure form or as a mixture solids, in which the microcapsules are admixed and which may be dissolved, suspended or dispersed evenly in a liquid medium, e.g. water, prior to application onto the target. Solid vehicles may for example be in the form of powders.

The term "liquid vehicle" refers to a pure liquid, to a homogeneous liquid mixture of agents (each of which before mixing may be a solid, a liquid, or a gas) or to a heterogeneous mixture of such agents, e.g. suspension, in which said encapsulated essential oils e.g., microcapsules, may be suspended. The suspension of the microcapsules in the liquid vehicle or in a solution (e.g., that is prepared by dissolving or dispersing a solid vehicle in an appropriate medium, as for example water), should be such that the consistency, distribution, physical state, or concentration of the volatile essential oil within the microcapsule is not affected. Such vehicle additionally is one in which said microcapsules do not dissolve, deteriorate, decompose, leach out or undergo any other physical or chemical transformation.

The term "suspended" or any lingual variation thereof refers to a state of dispersion of the microcapsules in the vehicle; by way of a non-limiting example the dispersion is of cottonseed oil and microcapsules in water. The term may alternatively refer to a state of colloid, depending on the size of the microcapsules.

In its most general form this invention discloses the encapsulation of one, or a mixture of essential oils with varying activities based on the specific applications.

The non-volatile vehicle may be at least one non-volatile essential oil, at least one non-volatile botanical oil or any combination thereof wherein at least one of the essential oils has the desired activity needed to exert the desired effect. For example, in case of a formulation which is used as a repellent of insects, one of the essential oils contained therein has repellent capabilities.

The combinations may for example be, without being limited thereto: (a) a combination of two or more different non-volatile essential oils; (b) a combination of two or more different non-volatile essential oils with at least one botanical oil; (c) a combination of one non-volatile essential oil with one non-volatile botanical oil; (d) a combination of two different non-volatile botanical oils, and the like. Similar variations may also be made with any one specific sub-group, e.g. lipids and with any one specific representative thereof, as for example different triglycerides.

The terms "volatile", "moderately volatile" and "non-volatile" refer to the degree of evaporative ability of a compound under ambient temperature and pressure. As is known to a person skilled in the art, the lower is the boiling point of a certain compound, the more volatile it is. In reference to essential oils, the volatile, low boiling point oils are those defined as having boiling points lower than about 250° C. The moderately volatile oils are those defined as having boiling points of between 250° C. and 300° C. The non-volatile or less volatile oils are those defined as having boiling points higher then 300° C.

"Botanical oils" are natural complex mixtures of oils made by plants. "Essential oils" are those that in general give to the plants their characteristic odors, flavors, or other such properties. Botanical oils are found in various parts of the plant body (in the seeds, flowers, bark, or leaves) and are also concentrated in certain special cells or groups of cells (glands). In general, they are complex mixtures that may be obtained from the plant in various ways, depending upon the nature of the part in which they are found. Such methods may for example be by compression, by distillation with steam, by dissolving the oils out (extraction) or absorbing them, and by pressure and maceration. The term also refers to oil mixtures prepared by enriching naturally obtained botanical oil with one or more specific component such as monoterpenes, diterpenes, triterpenes, tetraterpenes, sesquiterpenes, and other polyterpenes as well as organic alcohols, aldehydes ketones, acids and esters.

While the terms "essential oils" and "botanical oils" are used in different literary sources interchangeably, within the scope of the present invention the latter refers to a larger group of compounds that also includes lipids.

"Lipids" as referred to herein include the fatty acids, the glycerol-derived lipids (including the fats and oils and the phospholipids), the sphingosine-derived lipids (including the ceramides, cerebrosides, gangliosides, and sphingomyelins), the steroids and their derivatives, the terpenes and their derivatives, certain aromatic compounds, and long-chain alcohols and waxes. The term also refers to lipoproteins (lipids conjugated with proteins or carbohydrates), to lipopolysaccharides and to vitamins such as fat-soluble vitamins.

In a preferred embodiment, the oils are selected from sesame oil, pyrethrum, glycerol-derived lipids or glycerol fatty acid derivatives and the said at least one encapsulated essential oil is selected from cinnamon oil, cedar oil, clove oil, geranium oil, lemongrass oil, mint oil, sesame oil, thyme oil, turmeric oil, wintergreen oil, rosemary oil, anise oil, cardamom oil, chamomile oil, coriander oil, cumin oil, dill oil, mint oil, parsley oil, basil oil, camphor oil, citronella oil, *eucalyptus* oil, fennel oil, ginger oil, grapefruit oil, lemon oil, mandarin oil, orange oil, pine needle oil, pepper oil, rose oil, sweet orange oil, tangerine oil, tea tree oil, tea seed oil, lavender oil, caraway oil, garlic oil, peppermint oil, onion oil and spearmint oil.

In one embodiment, the essential oil is a volatile oil. In another embodiment, the essential oils is selected amongst citronella oil, geranium oil, tea tree oil, lavender oil, clove pine oil, *eucalyptus* oil, thyme oil, oregano oil, and other spice plant essential oils.

In another embodiment, the formulations may also comprise additives such as adjuvants, adhesives, antioxidants, water-resistant agents, surfactants, steric barrier polymers which prevent microcapsule aggregation and gel-breaking agents, as part of the vehicle or within the microcapsule.

Adjuvants may be used for example to improve shelf life, sprayabillity, and adsorption to the substrate. Such adjuvants may be chosen from both natural and synthetic polymers such as polyvinyl alcohol, polyvinylpyrrolidone, polyethylene oxides, ethylene or maleic anhydride copolymers, methyl vinyl ether-maleic anhydride copolymer, water-soluble cellulose, water soluble polyamides or polyesters, copolymers or homopolymers of acrylic acids, water-soluble starches and modified starches, natural gums such as alginates, dextrins and proteins such as gelatins and caseins.

The physical state of the formulation, namely as a solid or liquid, depends on whether the non-volatile vehicle is a liquid or a solid or whether the non-volatile vehicle and microcapsules are suspended or dispersed in an immiscible media such as water. Regardless of its physical state, the formulation may be put to use by further forming it into a desirable preparation form, such as an emulsifiable concentrate, a wettable powder, a granular wettable powder, a flowable preparation, a suspension, a granule, a dust, a fumigant and the like. The nature of the preparation form may be decided based on such parameters as the target environment, the method of application, the conditions under which the application is performed, the relative concentration of the microcapsules in the non-volatile vehicle, etc.

Although the concentration of the microcapsules in the non-volatile vehicle may be controlled, the concentration of the encapsulated essential oil may vary depending on storage, climate conditions, preparation form, method of application, place of application, objective insects to be controlled, and the like. The concentration of volatile essential oils within a formulation may vary between 0.01 to 90%, or preferably from 0.1 to 25%. However, the concentration of essential oils needed to achieve an effect after application is much smaller. This concentration may be appropriately selected from a range of 0.1% and preferably 0.25% in terms of weight of volatile essential oil.

The formulations may be adaptable to the two profiles of microcapsule release, namely (1) a rapid release profile; (2) and a sustained or a delayed release profile; and (4) a residuality profile in which the so-called "rapid release" is followed by a sustained release profile.

As stated hereinbefore, the formulations employed make use microcapsules which may be prepared by any of the methods disclosed or claimed herein. The microcapsules may be recovered from the reaction mixture and re-suspended in a non-volatile vehicle or in a solution containing thereof, e.g., for the purpose of producing a heterogeneous formulation. Alternatively, any medium, aqueous or otherwise, which comprises the microcapsules, may be treated with at least one non-volatile vehicle without separating the microcapsules.

In cases where the separation of the microcapsules from the initial medium is preferred, the recovery may be achieved, depending on the microcapsule size, by centrifugation or filtration. The isolated microcapsules may be washed with several portions of an appropriate solvent, e.g., distilled water, to remove free reactants from the surface. If necessary, the microcapsules may also be heated under reduced pressure to further remove any residual reactants from within the microcapsules. Preferably, this procedure is carried out by heating the microcapsule at a temperature above the median glass transition temperature of the polymer making up the microcapsule shell. These microcapsules may next be dispersed or suspended in said non-volatile liquid or solid vehicle.

The aforementioned heterogeneous formulations may be prepared by first preparing two or more different microcapsules, as disclosed above, for example each type containing a different essential oil or mixture; separating the microcapsules from their original medium; and admixing them in the desired ratio and medium, thereby affording the heterogeneous formulation.

In some cases, said non-volatile vehicle is a particulate solid, e.g. powder, by which the dispersion is preferably done by admixing an effective amount of dry microcapsules. In some cases, said non-volatile vehicle is a liquid, and the suspension is preferably prepared by mechanically stirring an effective amount of the microcapsules in said vehicle. The term "effective amount" as used herein refers to an amount determined empirically, which exerts a desired effect as is described herein below.

The "aqueous preparation of encapsulated volatile essential oils" is a preparation manufactured by any process known to a person skilled in the art. Preferably said aqueous preparation of encapsulated volatile essential oils is a preparation manufactured in accordance with the process of the invention, or alternatively as disclosed and claimed in WO04/98767.

The process of WO04/98767 comprises generally the dissolving a di- or polyisocyante into an essential oil, emulsifying the resulting mixture in an aqueous solution containing a di- or polyamine, and/or a di- or polyhydroxy compound to effect encapsulation of said essential oil through interfacial polymerization, whereby there is formed a polyurea and/or polyurethane film, also termed "thin encapsulating film" or "encapsulating membrane", around the essential oil droplets, which film enhances the stability of said essential oil, reduces its evaporation rate and controls its release rate when applied to a substrate. The encapsulating membrane may be predominately either polyurethane or polyureas of or a combination of both polyurethane and polyurea encapsulating membranes. Multiple encapsulating layers may also be formed where for example one of the layers is a polyurethane and the second layer a poly urea. Alternatively additional layers may be of a wax material.

In the process of the present invention, said di- or polyisocyanate is preferably chosen from the group consisting of dicyclohexylmethane 4,4'-diisocyanate; hexamethylene 1,6-diisocyanate; isophorone diisocyanate; trimethyl-hexamethylene diisocyanate; trimer of hexamethylene 1,6-diisocyanate; trimer of isophorone diisocyanate; 1,4-cyclohexane diisocyanate; 1,4-(dimethylisocyanato)cyclohexane; biuret of hexamethylene diisocyanate; urea of hexamethylene diisocyanate; trimethylenediisocyanate; propylene-1,2-diisocyanate; and butylene-1,2-diisocyanate mixtures of aliphatic diisocyanates and aliphatic triisocyanates are tetramethylene diisocyanate, pentamethylene diisocyanate, hexamethylene diisocyanate and 4-(isocyanatomethyl)-1,8-octyl diisocyanate, aromatic polyisocyanates include 2,4- and 2,6-toluene diisocyanate, naphthalene diisocyanate, diphenylmethane diisocyanate and triphenylmethane-p,p',p"-trityl triisocyanate. Suitable aromatic isocyanates are toluene diisocyanate, polymethylene polyphenylisocyanate, 2,4,4'-diphenyl ether triisocyanate, 3,3'-dimethyl-4,4'-diphenyl diisocyanate, 3,3'-dimethoxy-4,4'diphenyl diisocyanate, 1,5-naphthalene diisocyanate and 4,4',4"-triphenylmethane triisocyanate, and isophorone diisocyanate. Preferred reagents are toluene diisocyanate (TDI) or 4,4" diphenyl isocyanate (polyisocyante).

However, in another method of forming the encapsulating membrane the encapsulating membrane may be formed between an alkanoic acid dissolved in the essential oil which is absorbed onto or into the solid particle which will form the core and then this alkanoic acid will react with a basic solution of a salt of a multivalent cations having a charge greater than +1, such as inorganic metal cations are those of Group II of the periodic table (e.g., the multivalent cations of Ca, Mg, Fe, and Al), that forms the encapsulating membrane around the solid core by a process of complexation.

In forming layers beyond the first encapsulating membranes waxes may be applied from a hydrocarbon or non aqueous solution. Examples of such waxes applied from hydrocarbon solvents such as petroleum ether and hexane and other such solvents that may be used to put on second or third coatings are paraffin waxes, mineral hydrocarbon waxes, animal waxes (e.g., Beeswax, Chinese, shellac, etc.), Vegetable waxes (e.g., carnauba and Castor wax, Japan waxes, Jojoba oil etc), Mineral waxes (e.g., peat waxes, etc), Petroleum waxes (e.g, paraffin and microcrystalline waxes), synthetic waxes (e.g., Polyethylene waxes—based on polyethylene, Fischer-Tropsch waxes, Chemically modified waxes—usually esterified or saponified, polymerized α-olefins etc).

In one preferred approach a solid porous material is used as the core and the essential oil or a mixture of essential oils or the said essential oils which also contains dissolved therein an monomer or oligomers which is one of the reactants of the interfacial polymerization reaction that forms the encapsulating membrane.

The mode of release of the essential oil from the microcapsule and the ensued effect on the treated target depends on the physical characteristics of the microcapsule. Generally, the active volatile essential oil is a liquid depot encapsulated by the microcapsule shell and which may be carried in a non-volatile vehicle, which enhances (either additively or synergistically) its exerted effect. Upon delivery of the formulation to the target, the release of the microcapsule content is believed to commence due to the concentration gradient of the volatile essential oils inside and outside of the microcapsule. This release process and its kinetics may be influenced by: (a) drying of the microcapsules; (b) contact with an aqueous media, e.g. water or rain, water reservoirs as discussed hereinbefore, which may change the permeability of the encapsulating shell and/or cause slow decomposition of the shell; (c) varying temperatures, particularly high temperatures; and (d) direct sun light. It may, however, be the case that none of these conditions are required or have any effect, as the release of the microcapsule content may be spontaneous and independent.

Antimicrobial Formulations

Background—

The effective management and maintenance of large dairy herds and the production of dairy products has been a major accomplishment. One health problem that causes significant economic problems relates to mastitis. Mastitis is an inflammation of the lactiferous duct system or mammary gland tissues caused by the invasion and proliferation of bacteria in the udder of a mammal (including humans). Once mammals get mastitis, the ability to synthesize milk is damaged by the inflammation. That is, the mammals start to secrete abnormal milk, and the number of somatic cells, for example, leukocyte in the milk increases. Also, the mammary gland cells are damaged so that they become atrophied with an increase in the connective tissue, resulting in decreased lactation.

Mastitis is a disease that affects about 15% to 20% of dairy animals throughout the world. In the United States, it is thought that 50% of cows have one or more infected quarters. In Europe, it is estimated that mastitis is the cause of 30% to 40% of veterinary interventions. Mastitis is also common in women.

Bacterial infection, particularly bovine mastitis, is the most costly and difficult problem that a dairy herdsman will typically have to deal with. The dairy farmer is faced with two different types of mastitis infections, contagious and environmental. Contagious mastitis is spread during the milking process through contact between the animal and dairy equipment that may carry a source of a mastitis pathogen. Environmental mastitis is caused by contamination of the animal skin by materials from the barnyard environment, fields, barn interior, etc, as the animal moves through its environment.

Contagious mastitis is most easily controlled by using germicidal post milking teat dip compositions. Such germicidal dips kill bacteria that are introduced onto the surface of the animal from the milking machines. Environmental mastitis is best treated with a barrier film that protects sensitive tissues from contamination.

Mastitis may exist in varying levels of intensity, ranging from no observed symptoms to inflammation of the teat, high fever, weak and dejected animal, and lack of appetite. Such cases indeed result in the drastic drop in milk yield.

Microorganisms are responsible for the infection, but for them to enter the mammary glands and establish themselves to the point they cause an infection, a multitude of factors may be involved. There are many such factors (e.g., hygiene, housing, climate, milking machines, feed, genetics) acting simultaneously.

There are a great number of microorganisms on and in cow udders. In fact, 137 species and subspecies of microbes that can be associated with the mammary gland of the cow have been identified; several of which are part of the normal flora and, with few exceptions, do not cause mastitis. On the contrary, they may protect udders from infection caused by pathogenic bacteria.

Several other microorganisms may, however, cause infection in the mammary glands. The most common, those that cause about 90% of mastitis infections, are *Streptococcus agalactiae, Staphylococcus aureus, Streptococcus dysgalactiae, Streptococcus uberis, Escherischia coli*, and *Corynebacterium pyogenes*.

There are contagious microorganisms and environmental microorganisms. Infected cows are the main source of contagious microorganisms, which survive and proliferate on the skin and on teat wounds. They consist of *Streptococcus agalactiae, Staphylococcus aureus* and *Streptococcus dysgalactiae*. Environmental microorganisms (*Escherischia coli* and other coliforms, *Streptococcus uberis*) do not remain on the teat. Rather, their presence indicates a high degree of contamination of soil, bedding, and water caused, particularly, by manure.

Various preventive methods have been used to avoid the disease in both human subjects and non-human subjects. Such may include high hygiene, fore-milking to wash off or limit the collection of bacteria and other microorganisms which may be situated at the opening of the teat and thus may be washed by the foremilk, etc.

One class of compositions used in the treatment and prevention of mastitis is formed from aqueous coating systems. These coatings reduce the incidence of infection of the animal through the presence of an active biocide. However, these teat dips are easy to remove. For example, polyvinyl alcohol based teat dips do not provide adequate water resistance. That is, due to exposure to water, these films wear off in about 3 to 4 hours. Without an adequate barrier film the dairy animal is vulnerable to environmental pathogens, which will promote mastitis in the herd.

Another class of coating materials is characterized by the formation of film barriers on the skin surface to prevent contact between vulnerable tissues and the environment. Many antimicrobial materials are incompatible with a variety of these film-forming or polymeric materials. For example, antimicrobials cannot be used efficiently with latex since the antimicrobial material eventually precipitates out of the latex. Moreover, latex does not provide long-lasting coverings to the mammalian skin. Recent product developments provide coatings for teat skin that form film barriers, as well as, contain antimicrobial agents. Such coatings include solubilized liquids, polyvinylpyrrolidone and other vinyl polymers, protein hydrozylate, natural and synthetic gums, water, ethanol, methanol, isopropanol, soluble polymers, unsaturated fatty oils, cellulose derivatives, acrylic polymer lattices, etc.

Clay poultice, homeopathic remedies, medicinal plants and oxygen therapy may be used as curative methods against mastitis. The use of antibiotics has been suggested and used for the treatment of diseased animals. However, it is far from being the ideal solution. Other than the problems antibiotics cause with the milk (contamination from antibiotic residues, problems associated with yogurt and cheese processing, etc), antibiotics have not reduced the incidence of mastitis since their introduction as a possible solution. Problems associated with resistance or even ineffectiveness are quite real in the case of mastitis caused by coliforms and *Staphylococcus aureus*.

U.S. Pat. No. 6,106,838 to Nitsas discloses an antimicrobial composition comprising as an active ingredient an essential oil obtained from *Origanum vulgare* ssp. *hirtum* containing thymol and carvacrol as its main ingredients. This composition is used in the treatment of a variety of diseases caused by pathogenic microorganisms, including chronic mastitis or mastitis caused by *Staphylococcus* or *Streptococcus*.

U.S. Pat. No. 6,649,660 to Ninkov discloses pharmaceutical compositions which include oil extracts from plants from the Labiatae family for the treatment of microbial infections. U.S. Pat. No. 6,921,539 also to Ninkov similarly discloses therapeutic antimicrobial compositions and methods for their use in the treatment of such diseases as mastitis.

The above publications do not disclose the use of encapsulated essential oil formulations which exhibit both preventive and therapeutic properties.

DETAILED DESCRIPTION OF THE INVENTION

Summary—

There exists the need in the industry for antiseptic pre- and post-milking formulations that are highly effective skin decontaminants for the prevention of mastitis and which at the same time, leave the udder and teat skin in good condition for milking at either low or high frequencies. In addition, such compositions should provide a rapid kill of mastitis-causing microorganisms and be water-soluble, non-toxic and non-sensitizing. Such compositions would benefit dairies that milk at low frequency, and eliminate one of the major impediments to further practical development of high-frequency milking dairies.

It has now been determined, that the formulations comprising encapsulated essential oils prepared by the method of the invention or by interfacial polymerization may be used for combating microbial infections such as mastitis and thus are useful in preventing, controlling and treating the microbial-related disease or disorder.

There is, thus, provided an antimicrobial formulation comprising at least one encapsulated essential oil microcapsule prepared according to the novel method of the invention, or by interfacial polymerization as disclosed hereinabove, wherein said formulations is effective in treating or preventing a disease or disorder associated with at least one microbial pathogen.

The term "treating" as used herein refers to the application of an amount of the formulation containing volatile essential oils according to the invention which is effective in ameliorating undesired symptoms associated with the disease or disorder, preventing the manifestation of such symptoms before they occur, slowing down the progression of the disease or disorder, slowing down the deterioration of symptoms associated with the disease or disorder, slowing down the irreversible damage caused by the pathogens, lessening the severity or cure of the disease or disorder, ensuing a more rapid recovery, or preventing the disease form occurring or a combination of two or more of the above.

In one embodiment, the microbial pathogen is selected from *Escherichia coli, Staphylococcus Aureus, Micrococcus* CNS, *Streptococcus Dysgalactiae, Areanobacterium Pyrogenes*, and *Pseudomonas Aeruginos*.

In another embodiment, said antimicrobial formulation is for treating or preventing mastitis in milking animals and humans.

In another embodiment, said antimicrobial formulation is an antiseptic formulation.

Also provided is a method for modulating mastitis in milking animals, said method comprising applying onto said animal's teat an antimicrobial essential oil formulation, said formulation being optionally capable of forming a barrier layer, thereby substantially preventing the entry of microbes into the udder.

The term "modulating" as used herein refers to the application of an amount of the formulation containing volatile essential oils according to the invention which is effective in ameliorating undesired symptoms associated with mastitis, preventing the manifestation of such symptoms before they occur, slowing down the progression of mastitis, slowing down the deterioration of symptoms associated with mastitis, slowing down the irreversible damage caused by the pathogens, lessening the severity or cure mastitis, improving milking or more rapid recovery, or preventing the disease form occurring or a combination of two or more of the above.

Also provided is a method for reducing microbial population on a surface or an object, said method comprising applying onto said surface or object an antimicrobial essential oil formulation, optionally being capable of forming an antimicrobial barrier layer.

In one embodiment, said surface or object is a milking animal's teat.

The term "milking animal" refers to an animal that is considered a dairy animal. Such animals may be cows, goats, camels, alpacas, etc. However, such formulations may be effective also in the treatment of mastitis in milking animals which milk is typically not part of the human diet. The term also refers to humans.

The formulations employed may be heterogeneous or homogenous. Additionally, the microencapsulated essential oils may be presented to the target along with a high boiling (active or non-active) vehicle, as disclosed by the inventors of the present invention in U.S. application Ser. No. 11/040, 102, incorporated herein in its entirety.

In another embodiment, said formulation comprises at least one encapsulated antimicrobial essential oil and at least one non-encapsulated essential oil, acting as the carrier.

Preferably, said antimicrobial essential oil is one or more of oregano oil, basil oil, rosemarin oil, *eucalyptus* oil, tea tree oil, or thyme oil.

Other essential oils, which may be encapsulated, are those obtainable from the Lamiaceae, Labiatae, or Verbenaceae families.

The formulation which is capable of forming a barrier layer may further comprise a polymer which upon application to the skin of the animal dries to form said barrier. Alternatively, the formulation may comprise at least one monomer which polymerizes upon drying or in the presence of an initiator to form the polymer barrier.

In one embodiment, the antimicrobial barrier formed after application of the formulation of the invention is based on a polymer or a monomer being contained within the essential oil formulation. In another embodiment, the polymer or monomer is not contained within the formulation but is applied onto the skin following application of the essential oil formulation, before application or in a mixture prepared immediately before application.

The essential oil formulation used for the modulation of the microbial-related disease such as mastitis or for reducing microbial population, may further comprise other antibacterial agents commonly used to control or treat the disease, e.g., mastitis. Such combination may result in a more effective antimicrobial activity which may also exhibit a prolonged effect or a broader effect on a greater variety of microbes. Additionally, such combination may significantly reduce the effective concentration of the said antibacterial formulation. Thus, such formulations may be used to modulate both the contagious and environmental forms of mastitis.

Without being limited thereto, the additional antimicrobial agent may be selected from stabilized chlorine such as chlorine dioxide, chlorhexidine salts, chlorine release compounds such as alkali hypochlorites, oxidizing compounds such as hydrogen peroxide and peracids; protonated carboxylic acids (i.e. fatty acids) such as heptanoic, octanoic, nonanoic, decanoic, undecanoic; acid anionics such as alkylaryl sulfonic acids; quaternary ammonium salts, and iodine.

The formulations of this aspect may be applied to the teats of the milking animals by any known method such as spraying, brushing, swabbing or foaming onto the teats, and at any time during the milking period. The formulations may also be applied by dipping (so-called teat-dip application) the teat into a reservoir or receptacle containing the formulation of the invention.

After application, the teats that have been covered by the formulation are allowed to dry, at which point the antimicrobial barrier and prophylactic shield form.

In one embodiment, the formulation may be sprayed on the animal's udder immediately after milking when the teat is most susceptible to infection and may be removed from the animal's udder prior to the next milking. Such post-milking application may prevent entry of pathogens into the teat immediately after milking, as the teat-end sphincter muscle (responsible for closing the teat-end) remains open for approximately 30 minutes after milking.

In another embodiment, the anti mastitis formulation may be applied at the start of and during the dry period when milking in not carried. It could be applied periodically to the udder throughout the dry period to prevent and control mastitis. An essential part of a mastitis control program is the dry cow therapy. Dry cow therapy is treatment of a cow during the approximately four to ten-week period immediately preceding the delivery of a calf. This period is also known as the non-lactating period. Although during this period the mammal is not exposed to potential contamination form milking machines, forty to fifty percent of teat infections occur during this period. This high rate of infection occurs since a mammal's immune response is diminished during the dry period. Additionally, the teat is distended during the dry period allowing more facile microbial penetration into the mammary gland and without the flushing lactation, the likelihood of infection increases. Thus, treating a dairy animal during its dry period should also minimize the rate of infection.

Example 1

A solution of 35 g tolylene diisocyanate (TDI) mixed into 250 g of an essential oil (Table 1) was added into 500 g water containing 5 g polyvinyl alcohol (PVA) using a high sheer mixer. To this were added 120 ml of water with 55.6 g polyethylene glycol (PEG) 4000. The mixing was continued for two hours at room temperature. The emulsion which resulted was treated with 12 g Guar gum and 4 g of a Nefocide. To break up the hydrogel consistency of the emulsion, 10 g of 1% sodium dodecyl sulfate (SDS) were added.

The formulation was next tested on a variety of microorganisms in order to evaluate its antimicrobial efficacy, particularly in treating mastitis.

Generally, the formulation was found to be an efficient antimicrobial formulation, having efficacy against all the pathogens tested.

Example 2

10 g of an essential oil with 12 g stearic acid dissolved therein were added to a rapidly stirring (high speed shear stirrer) solution of 250 ml $H_2O$ with 2.5 g polyvinyl alcohol (PVA). To this, a solution of 22.8 g hexahydrate $CaCl_2$ in 20 ml $H_2O$ was added and stirred for two hours. Next, 1.5 g methyl paraben, 8 ml Latron B 1956 and 3 g Guar gum were added with continual stirring for another 2 hours. Microcapsules containing other essential oils were prepared similarly:

1—Tea tree oil encapsulated in Lauric acid by $CaCl_2$;
2—Thyme oil encapsulated in stearic acid by $CaCl_2$;
3—*Eucalyptus* oils encapsulated in stearic acid by $CaCl_2$ with free Pyrethrum and Sesame oil;
4—Oregano oil encapsulated in decanoic acid by $CaCl_2$ with free Pyrethrum and Sesame oil;
5—Tea tree oil encapsulated in decanoic acid by $FeCl_2$;
6—Citronella oil encapsulated in Lauric acid by $MgCl_2$ with free Pyrethrum and Sesame oil;
7—Tea tree oil encapsulated in decanoic acid by $MgCl_2$.

In-Vitro Tests:

Samples of the following pathogenic bacteria received from the Israeli Dairy Board (Production and Marketing) were used to test the efficacy of the above formulation:
a) *Escherichia coli*,
b) *Staphylococcus Aureus*,
c) *Micrococcus* CNS,
d) *Streptococcus Dysgalactiae*,
e) *Areanobacterium Pyrogenes*, and
g) *Pseudomonas Aeruginos*.

Each of the different bacteria was grown on TSBA and sheep's blood plates at 37° C. for 18 hours. *Arcanobacterium Pyrogenes* was grown at 30° C. for 42 hours. Next, the bacteria were washed from the plates with 0.9N sterile saline and suspended in sterile saline. The concentration of the bacterial suspension was adjusted to approximately $5 \times 10^8$ CFU/ml.

To the suspension, essential oil formulations containing oregano oil, tea tree oil, or thyme oil were applied. Varying concentrations of the essential oil formulations were used, ranging from 0.01% to 1%. Common volume of inoculum bacteria with oil formulation was 5 ml.

After vortexing the mixture of the inoculum and essential oil formulation for 10 minutes, the mixture was filtered through a sterile glass microfilter (GF/C 1.2 microns from Whatman filter company) using a vacuum pump.

The liquid filtrate was diluted and transferred to a TSBA and sheep's blood plate. The plate was incubated at the optimal temperature for 18-42 hours; thereafter the colony of bacterial on each plate was counted.

The results are summarized in Tables 1 and 2 below:

TABLE 1

Summary of antibacterial efficacy of different formulations of essential oils encapsulated according to the procedure of Example 1.

| Formulation Bacteria Type/CFU | Tea tree | Thyme | Oregano |
|---|---|---|---|
| | MIC Concentration (%) (Bacterial counts per 1 ml) | | |
| *Escherichia Coli*/$2 \times 10^8$ | 0.05 | — | 0.02 |
| *Staphylococcus aureus*/$4 \times 10^8$ | 0.2 | — | 0.1 |
| *Pseudomonas aeruginosa*/$8 \times 10^8$ | 0.2 | — | 0.02 |
| Micrococcus CNS/$5 \times 10^9$ | 0.4 | 0.4 | 0.2 |
| *Streptococcus Dysgalactiae*/$2.5 \times 10^8$ | 0.08 | 0.08 | 0.2 |
| *Areanobacterium Pyrogenes* | 0.08 | 0.08 | 0.08 |
| Nature of encapsulation | Polymeric envelope Polyurethane | Polymeric envelope Polyurethane | Polymeric envelope Polyurethane |

TABLE 2

Summary of antibacterial efficacy of different formulations of essential oils encapsulated according to the method of Example 2.

| Formulation Bacteria Type/CFU | Tea tree | Tea Tree |
|---|---|---|
| | MIC Concentration (%) (Bacterial counts per 1 ml) | |
| *Escherichia Coli*/$2 \times 10^8$ | 0.1 | 1.0 |
| *Staphylococcus aureus*/$4 \times 10^8$ | >0.6 | >0.8 |
| *Pseudomonas aeruginosa*/$8 \times 10^8$ | 0.8 | 1.0 |
| Nature of encapsulation | Stearic with $CaCl_2$ | Lauric acid with $CaCl_2$ |

Example 3

Essential oils such as tee tree oil, *eucalyptus* oil, oregano oil, essential oils obtained from thyme, essential oils from the herbs of the genus *origanum* and other essential oils of plant species that of the Lamiaceae, Labiatae, and Verbenaceae families were also encapsulated according to the method of Example 2.

These essential oils were also encapsulated by interfacial polymerization as disclosed in Example 1. Mixtures of microcapsules containing polyurethane microcapsules and polyurea microcapsules, each with a different release profile to give a wider range of release profiles for the formulation were also prepared.

Repellency and Extermination of Insects

Background—

Unlike insecticides which may exert their effect only after the insects have settled on the target, thereafter stinging with the possibly resulting immediate or delayed infection, insect repellants prevent harmful insects from flying in or touching and from stinging and sucking on surfaces attractive to them, as for instance the skin of animals and humans. In many areas, the driving off of stinging, blood-sucking and other bothersome insects is an urgent need, because they may in part also transmit diseases. Active substances for driving off such insects, therefore, have an important sanitary, hygienic and cosmetic function to fulfill.

Insect repellants are widely used throughout the United States and throughout the world. In some regions, the use of insect repellants is critical to avoiding or reducing the occurrence of disease carried by insects. For example the Centers for Disease Control (CDC) receives nearly 101,000 reports of Lyme disease (transmitted by deer ticks) and 1,000 reports of encephalitis (transmitted by mosquitoes) annually.

Numerous effective repellants are known in the art. One of these, N,N-diethyl-m-toluamide (DEET) has been shown to be excellently effective as a mosquito repellant and is currently considered one of the most commonly used. DEET was designed to be applicable to the skin of subjects, and to repel rather than kill insects. A number of compositions containing this material are commercially available for use on humans and animals, for instance in the form of creams or aerosol compositions.

Concerns have recently been raised as to the potential toxicity of long-term use of DEET and other available pest repellants to children. At present, it is forbidden to use DEET on children below the age of seven. Recently the US Environmental Protection Agency (EPA) determined that it would no longer allow child safety claims on labels for DEET-containing products. In addition, although DEET is effective as a repellant, it has the dual disadvantage that it must be used in relatively high concentrations and, more importantly, it is not effective for affording continuous protection against pests for more than about six hours.

Numerous encapsulated insect repellents in time control release agents have been reported. Examples of such repellent systems are disclosed in U.S. Pat. No. 4,548,764 to Munteanu et al., and U.S. Pat. No. 5,069,231 to Rutherford. Such repellent encapsulation systems have very limited effectiveness overtime and are typically effective for less than one week. Highly volatile materials such as esters, ethers, and aldehydes are commonly found in available compositions which make these compositions inherently unstable and therefore require the presence of chemical stabilizers.

Another available repellant for repelling small blood-feeding pests from the skin, hair, or fur of a mammal is cyano(3-phenoxyphenyl)methyl-4-chloro-alpha-(1-methylethyl)-benzeneacetate. The active compound is conveniently formulated into compositions which are adapted to topical application to the skin, hair, or fur of a mammal (see for example U.S. Pat. No. 4,547,360).

Essential oils have also been used in repelling insects. Lavender oil, for example, was used to protect children from head lice infestation. Recently piperonal (1,3-benzodioxol-5-carboxaldehyde) was introduced as a repellent to the market. Citronella candles used to repel insects have also been manufactured, despite the showing that citronella oil is not a very effective insect repellent even when released into the air from a candle. Even commercially available topical compositions containing citronella oil are not very effective, probably due to the fact that they work for a very short period of time, i.e., 10-20 minutes or less if the subject perspires, and due to the need to cover the whole body if a complete repelling effect is sought.

The use of essential oil based formulations in agriculture has also been reported. PCT Publication No. WO 04/098767 to the inventors of the present invention discloses microcapsules of essential oils which may be used, among other applications, as pesticides, insect repellents, and as antiviral or antifungal agents. When the microcapsules are applied to given substrates, the essential oil contained therein is released at a constant rate over a period of time. The efficacy of such microcapsules depends on the potency of the encapsulated material and parameters relating to the microcapsules themselves, i.e., size, thickness of the encapsulating membrane, ability to sustain release of the essential oil contained therein, etc., and not on the aqueous medium which carries them to the target environment which dries immediately thereafter.

U.S. application Ser. No. 11/040,102 to the inventors of the present invention discloses encapsulated essential oil formulations which comprise at least one encapsulated volatile essential oil and a non-volatile vehicle in which said at least one volatile essential oil is carried. Such formulation is used for the management of pest populations in agricultural environments.

Summary—

It has now been found that the essential oil formulations such as those manufactured in accordance with the methods of U.S. application Ser. No. 11/040,102, or the method of the present invention, may be used for repelling or exterminating insects from the skins of animals or humans or from surfaces and objects on which they may land or to which they may be attracted. Such insects are capable of causing annoyance or injury to animals or humans and may for example be mosquitoes, ticks, flies, ants and cockroaches. It has been further discovered that such a formulation may be applied directly to the skin of such animals or humans or to in-door or out-door surfaces which may be in contact or in close proximity to animals or humans.

The formulations of U.S. application Ser. No. 11/040,102, for example, which comprise encapsulated volatile essential oils (e.g., citronella) and non-volatile essential oils as vehicles (e.g., pyrethrum) and which may further comprise active agents such as the insect growth regulator, Novaluron, (contained with the encapsulated essential oil, in the vehicle, or both) have demonstrated their efficacy in repelling or exterminating insects from wet or humid environments such as natural or artificial water reservoirs such as fish tanks, lakes, aquariums, drinking water reservoirs, and other aquacultures.

It has also been determined that the repellent/exterminating formulations may be used to achieve one or more of the following advantages over an existing insect repellent available for similar purposes:

1. They may be more effective then those commercially available for application onto human skin;

2. They significantly reduce insect population within the treated area, thus eliminating or significantly reducing the use of skin contact formulations;

3. They more effectively reduce the spread of diseases or nuisances by mosquitoes and other insects;

4. They may be used in conjunction with skin formulations in heavy mosquito or insect infestations for a synergistic affect;

5. They may be used to reduce pest population in animal areas such as kennels, barns and circuses without application to individual animals; and 6. They may be applied in the vicinity of children, thus obviating the use of direct contact and ensue of side effects to which children are more prone to than adults.

Thus, in another aspect of the present invention there is provided a repellant or insecticidal formulation for reducing the population of insects in a treated non-agricultural environment, said formulation comprising at least one encapsulated volatile essential oil and a non-volatile vehicle in which said at least one volatile essential oil is carried. The non-volatile vehicle may be a solid or a liquid vehicle.

In one embodiment, the formulation of encapsulated essential oil is prepared according to the method of the invention. In another embodiment, the formulation of encapsulated essential oil is prepared by interfacial polymerization.

In another embodiment, said insect is capable of causing annoyance or injury to animals or humans. Such insects may be, without being limited thereto, selected from mosquitoes, ticks, flies, ants and cockroaches.

In another embodiment said non-volatile vehicle is selected from the group of non-volatile essential oils, non-volatile botanical oils or any combination thereof.

When the formulation is made suitable for direct application onto the skin of animals or humans it may further comprise at least one pharmaceutical or cosmetic agent which may provide additional benefit when applied to the skin (e.g. menthol, vanillin).

For human or animal use, the essential oils may be selected from: peppermint oil, clove oil, *eucalyptus* oil and lavender oil; anise oil, *angelica* oil, iris oil, fennel oil, orange oil, *cananga* oil, caraway oil, cardamom oil, guaiacwood oil, cumin oil, *Lindera* oil, cinnamon oil, geranium oil, copaiba balsam oil, coriander oil, *perilla* oil, cedarwood oil, citronella oil, jasmine oil, palmarosa sofia oil, cedar oil, spearmint oil, Western mint oil, star anis oil, tuberose oil, clove oil, Neroli oil, wintergreen oil, tolu balsam oil, patchouli oil, rose oil, palmarosa oil, *Chamaecyparis obtusa* oil, Hiba oil, sandalwood oil, petitgrain oil, bay oil, vetivert oil, bergamot oil, Peru balsam oil, bois de rose oil, camphor oil, mandarin oil, *eucalyptus* oil, lime oil, lavender oil, linaloe oil, lemongrass oil, lemon oil, rosemary oil, and Japanese mint oil.

Essential oils which may be encapsulated in formulations directed at repelling insects from human or animal skin may be selected from almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, *eucalyptus* oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen.

Examples of active ingredients in essential oils are: citronellal, methyl salicylate, ethyl salicylate, propyl salicylate, citronellol, safrole, and limonene, Organo, citronella and lavender, geranium oil, rosemary oil and peppermint oil spearmint oil, pine needle oil and *eucalyptus* oil. Less suitable, but still effective are lemon oil, grapefruit oil, lavandin oil, cinnamon oil, clove oil, thyme oil, wintergreen oil, cedar oil, lemon grass oil, mandarin oil, tangerine oil, orange oil, citrus oil, lime oil, coriander oil, pomegranate oil, walnut oil, peanut oil, corn oil, canola oil, sunflower oil, sesame oil, linseed oil, safflower oil and olive oil.

Essential oils which may be used in formulations for use as larvicide and insecticide and which are suitable to human and animal use may be selected from pine pyrethrum, tea tree, thyme and essential oils that come from these families—alpha-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, dimethyl salicylate, eucalyptol (cineole), eugenol, iso-eugenol, galaxolide, geraniol, guaiacol, ionone, d-limonene, menthol, methyl anthranilate, methyl ionone, methyl salicylate, alpha-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil (white and red), thymol, trans-anethole, vanillin, ethyl vanillin, and the like.

Also useful are rosemary oil and/or wintergreen oil that can be used with plant essential oils such as thyme oil, eugenol and 2-phenethyl propionate, carvacrol and beta-thujaplicine derived from *Thujopsis dolabrata* var *hondai* sawdust.

Additional agents may be selected from adjuvants, antioxidants, UV absorbers, surfactants, water soluble polymers, and non-water soluble polymers, solvents (e.g., alcohols) and the like.

The applicability of any one certain formulation as a repellent or an insecticide depends on the essential oil or essential oil combination used. One essential oil combination may be useful for only repelling the insects while the other may be efficient in exterminating them. The concentration of the essential oil formulation used may also have an effect on the repellency or extermination capabilities of the formulation.

The term "to repel" or any lingual variation thereof refers to the act of driving the insects off without ensuing their death. The term "to exterminate" or any lingual variation thereof refers to the act of killing a whole population of insects or any part thereof. The term "insect" refers to mosquitoes, ticks, flies, ants and cockroaches and other insects, nematodes, that cause annoyance or injurious to animals or humans.

The term "mosquito" as used herein concerns any type of mosquito, e.g., *Anopheles, Aedes,* and *Culex,* including but not limited to Tiger mosquitoes, *Aedes aborigines, Aedes Aegypti, Aedes, albopictus, Aedes cantator, Aedes sierrensis, Aedes sollicitans, Aedes squamiger, Aedes sticticus, Aedes vexans, Anopheles quadrimaculatus, Culex pipiens,* and *Culex quinquefaxciatus.*

The term "tick" as used herein includes any type of tick, including but not limited to, deer ticks, the American dog tick (*Dermacentor variabilis*), *Ornithodoros parkeri, O. moubata,* and *Dermacentor andersoni.* The term "cockroach" as used herein refers to any type of cockroach, including but not limited to the American cockroach (*Periplaneta americana*), German cockroach (*Blattella germanica*), oriental cockroach (*Blatta orientalis*), wood cockroach (*Parcoblatta pennsylvanica*), brownbanded cockroach (*Supella longipalpa*), and smokybrown cockroach (*Periplaneta fuliginosa*).

By repelling or exterminating the population of insects capable of inflicting damage to the target environment, the formulations may also assist in reducing damage caused by viruses, by limiting viral transmission by insect vectors.

The formulations may be prepared in various forms depending on the application, the environment treated, the concentration of the formulation applied and the degree of coverage (e.g. application to the whole skin or to the skin covering a specific organ). Such preparation forms may be, without being limited thereto, selected from emulsified concentrate, wettable powder, granular wettable powder, flowable preparation, suspension, granule, dust, fumigant, solution, sprayable preparation and aqueous solution.

The present invention further provides a method for repelling or exterminating an insect population capable of causing annoyance or injury to animals or humans, said method comprising applying to a non-agricultural environment or to an insect population in said environment a formulation comprising at least one encapsulated volatile essential oil and a non-volatile vehicle in which said at least one volatile essential oil is carried.

In one embodiment, the method involves direct application of the formulation onto the skin of animals or humans.

In another embodiment, the method involves application of the formulation onto surfaces such as floors, walls, ceilings, furniture, nets, screens, lawns, clothing, car seats, surfaces in animal husbandries, and aquacultures.

It has also been found in the course of the investigation leading to the invention of the present application, that the non-volatile vehicle enhances the repelling effect exerted by the volatile essential oil, and that the effect exerted by the non-volatile vehicle is enhanced by the volatile essential oil. Thus, the present invention further provides repellent formulations comprising each an effective amount of the formulation of the present invention.

In another embodiment, the formulation may also comprise in addition to the essential oil repellants at least one additive selected from insect growth regulators (IGR), insecticides, acaracides, fungicides, nematicides, and/or ectoparasiticides, either within the microcapsule or as part of the vehicle. Preferably, said formulation may contain at least one insecticide which are soluble in either said at least one encapsulated essential oil or in the non-volatile vehicle. Such insecticides may for example be carbamates, ureas, triazines, triazoles, uracils, organophosphates, morpholines, dinitroanilines, acylalaninies, pyrethroids, and organochlorines. Specific examples are carbofuran, azinphos-methyl, sulfentrazone, carfentrazone-ethyl, cypermethrin, cyromazine, beta-cyfluthrin, endosulfan, phosmet, chlorobromuron, chloroxuron, chlorotoluron, fluometuron, metobromuron, thiazafluron, teflubenzuron, hexaflumuron, diflubenzuron, flufenoxuron, lufenuron, chlorfluazuron, novaluron. dimethachlor, metolachlor, pretilachlor, 2-chloro-n-(1-methyl-2-methoxyethyl)-acet-2,6-xylidide, alachlor, butachlor, propachlor, dimethenamid, bifenox, 4-(4-pentyn-1-yloxy) diphenylether, acifluorfen, oxyfluorfen, fluoroglycofen-ethyl, fomesafen, cis,trans-(+)-2-ethyl-5-(4-phenoxyphenoxymethyl)-1,3-dioxolane, fluazifop-butyl, haloxyfop-methyl, haloxyfop-(2-ethoxyethyl), fluorotopic, fenoxapropethyl, quizalofop-ethyl, propaquizafop, diclofop-methyl, butralin, ethalfluralin, fluchloralin, isopropalin, pendimethalin, profluralin, trifluralin. aclalanines furalaxyl, metalaxyl, benzoylprop ethyl, flamprop methyl, difenoconazole, etaconazol, propiconazole, 1,2-(2,4-dichlorophenyl)-pent-1-yl-1h-1,2,4-triazole, triadimefon, dioxacarb, furathiocarb, aldicarb, benomyl, 2-sec-butylphenylmethylcarbamate, etiofencarb, fenoxycarb, isoprocarb, propoxur, carbetamid, butylate, di-allat, eptc, molinate, thiobencarb, tri-allate, vemolate, piperophos, anilofos, butamifos, azamethiphos, chlorfenvinphos, dichlorvos, diazinon, methidathion, azinphos ethyl, azinphos methyl, chlorpyrifos, chlorthiofos, crotoxyphos, cyanophos, demeton, dialifos, dimethoate, disulfoton, etrimfos, famphur, flusulfothion, fluthion, fonofos, formothion, heptenophos, isofenphos, isoxathion, malathion, mephospholan, mevinphos, naled, oxydemeton methyl, oxydeprofos, parathion, phoxim, pyrimiphos methyl, profenofos, propaphos, propetamphos, prothiophos, quinalphos, sulprofos, phemephos, terbufos, triazophos, trichloronate, fenamipos, isazophos, s-benzyl-o,o-diisopropylphosphorothioate, edinphos, and pyrazophos.

In another embodiment, the formulation of the present invention may be used against viral transmitting insects capable of acting as viral vectors for infection. The term "viral vector" refers to any such insect as defined and exemplified herein which is capable of carrying and transmitting a plant virus disease-causing, organism.

In another aspect of the present invention, there is provided a method for managing insect population, said method comprising applying to the target environment or to said insect population or to the loci thereof, a microencapsulated essential oil formulation as disclosed herein.

The term "non-agricultural target environment" as used herein generally refers to an environment which is different from agricultural or horticultural environments. The term, however, refers to in-door or out-doors environments from which the repelling or exterminating of insects is desired. Such may be rooms in a home, work offices, building interiors, gardens, schools, nurseries, public entertainment areas, sport stadiums, transportation areas like subway stations, airport terminals, boats yachts, cars, buses, trains and the like. Surfaces that may be sprayed are floors, walls, ceilings furniture, nets, screens, lawns, etc.

Since most of the insects capable of causing annoyance or injury to animals or humans find their habitat next to or in wet environments such as ponds, there exists the need to exterminate existing insect population from such wet environments, i.e., aquaculture, or to repel them therefrom.

In fact, it has been found that the formulations of the invention may be applied to various water reservoirs thereby achieving either extermination of existing populations of such insects or repelling opportunistic insects from the target water reservoirs. This avoids the need of using toxic and long-surviving chemicals which may create an environmental hazard to both the environment and to humans and animals using such water reservoirs on a recreational or as daily basis.

The term "water reservoirs" or "wet environment" refers herein to, without being limited thereto, water systems, cooling systems, swimming pools, natural and artificial water reservoirs, fisheries, water tanks, aquariums, irrigation systems and any other volume of water.

In one embodiment, the formulation is added in a dry form to the water reservoir in an amount sufficient to manage the insect population. In another embodiment, the dry composition is added to a water reservoir after being dissolved in an appropriate vehicle.

The formulations used in eradicating pests from water reservoirs may also be useful to control microorganisms and prevent root intrusion into the water source, particularly irrigation tubes.

Drip irrigation, from both above the surface and also from below, by a technique referred to as subsurface or low volume irrigation, is the process of delivering water and nutrients directly to the plant's root zone. Such water delivery affords exact irrigation control and efficient use of limited water resources. The ease by which such irrigation systems have been installed and the relatively low cost of installation has made subsurface irrigation the solution of choice of both private and municipal consumers for watering gardens and parks.

With the use of reclaimed water for watering of plants a properly engineered and managed subsurface drip irrigation system offers many advantages over conventional watering methods as such subsurface irrigation minimizes health risks associated with exposure to reclaimed water by distributing the water below ground.

One of the primary challenges of utilizing subsurface drip irrigation for long-term applications has been the potential for internal plugging of the irrigation systems and external root intrusion into the drip tubing. Numerous solutions have been proposed as solutions. For example, some use trifluralin to prevent root intrusion into the emitters, while others incorporate a root intrusion barrier directly into the tubing material itself.

While root intrusion into the drip lines and internal clogging from the buildup of sediment, suspended solids, algae and bacterial slime have been diminished greatly by better pretreatment, filtration disinfections, and new tubing and emitter designs, there exists the need for a unified method which would prevent both the intrusion of opportunistic roots and the build up of sediment due to growth of fungi and bacteria.

One of the biggest problems in aquaculture production and managing is the bacteria and fungi in the water which quickly multiply and kill fish and shrimps within a matter of hours or days. Application of the formulations disclosed herein to such aquacultures helps in controlling such fungi and bacteria and thus assists in maintaining a live and health stock.

Bacterial and fungal infestations may be controlled as discussed hereinbefore. Nematodes may also be controlled by applying to the soil an essential oil formulation of the invention which comprises a natural essential oil, which controls nematodes and their eggs.

It has now been discovered that incorporation of a formulation comprising encapsulated essential oils also into the water flow of subsurface irrigation systems allows a long-term control of microorganisms and prevents root intrusion into the tubing.

Thus, the present invention also provides a formulation comprising at least one essential oil which may be chosen from those with antimicrobial and/or fungicidal properties as disclosed herein for use in the control of microorganisms and prevention of root intrusion into irrigation tubings. Examples of such essential oils are tea tree oil, thyme oil, clove oil, *eucalyptus* oil, oregano oil, citronella oil, basil oil, oil of fennel and oil of anise.

In one embodiment, these essential oils may be used with mixtures of synthetic herbicides for root control. In another embodiment, essential oils with herbicidal properties used. These essential oils having herbicidal properties or synthetic herbicides may be encapsulated together or in different microcapsules.

The essential oils having herbicidal properties are those which comprise a monocyclic, carbocyclic ring structure having six-members and substituted by at least one oxygenated or hydroxyl functional moiety. Examples of plant essential oils encompassed within this definition, include, but are not limited to, members selected from the group consisting of aldehyde C16 (pure), amyl cinnamic aldehyde, amyl salicylate, anisic aldehyde, benzyl alcohol, benzyl acetate, cinnamaldehyde, cinnamic alcohol, alpha-terpineol, carvacrol, carveol, citral, citronellal, citronellol, p-cymene, diethyl phthalate, dimethyl salicylate, dipropylene glycol, eucalyptol (cineole), eugenol, iso-eugenol, galaxolide, geraniol, guaiacol, ionone, d-limonene, menthol, methyl anthranilate, methyl ionone, methyl salicylate, .alpha.-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, and the like.

These essential oils may also be used as carriers for encapsulated essential oils with antimicrobial and fungicidal activity.

The essential oils either for antimicrobial or/and fungicidal and/or herbicidal may be encapsulated together in the same microcapsules or made in separate microcapsules and then mixed.

The formulation of the present invention may be presented, stored, packed or applied as a single formulation, wherein the encapsulated volatile essential oil is pre-mixed with the non-volatile vehicle, or as a two-component formulation, which comprises the encapsulated volatile essential oil as one component, for example in a separate container or applied separately, and the non-volatile vehicle as a second component.

Thus, there is provided a method for managing insect population, said method comprising:
applying to the target a microcapsule formulation comprising at least one volatile essential oil, and
applying to the target environment a second formulation comprising a non-volatile agent.

The application of the second formulation may be done immediately after the application of the first formulation, or at any time thereafter. A person skilled in the art would be able to decide which of the two methods of managing insect populations disclosed herein is more suitable for the specific case.

The formulation disclosed herein may be delivered to the target by any method known to a person skilled in the art. Such methods may include for example: (a) manual or mechanical application of the formulation to a given surface by, for example, applying a liquid preparation either diluted or undiluted with water to said surface; (b) applying a granular agent such as dust or a wettable powder to the surface (c) ground or aerial spraying of a liquid formulation to the many gardens within a neighborhood or to specifically selected areas; (d) burying the formulation in the topsoil of a garden, etc.

A) Formulations Used for Repelling Mosquitoes

The following formulations were used for repelling mosquitoes from a variety of surfaces and indoor or outdoor locations:

Formulation 1: Citronella oil, lavender oil, geranium oil in a ratio of 1:1:1 dissolved in almond oil forming a 24% solution of the oils (purchased under the brand name Di-Tush™, Tamar Ltd., Israel) were microencapsulated in a polyurethane envelope by the procedure described in Example 1 below.

Formulation 2: Encapsulated Citronella oil and non-encapsulated pyrethrum and sesame oil.

Formulation 3: Encapsulated Citronella oil with Novaluron and non-encapsulated pyrethrum and sesame oil.

Formulation 4: Encapsulated Citronella oil with Novaluron and non-encapsulated pyrethrum and sesame oil and 20 mg Novaluron.

Formulation 5: Encapsulated Citronella oil with Novaluron and non-encapsulated pyrethrum and sesame oil and 10 mg Novaluron.

Formulation 6: Encapsulated Citronella oil with Novaluron and non-encapsulated pyrethrum and sesame oil and Novaluron.

Formulation 7: Encapsulated tea tree oil.

Formulation 8: Encapsulated tea tree and Novaluron with non-encapsulated pyrethrum and sesame oil.

Formulation 9: Pyrethrum Citronella oil Sesame oil encapsulated in Lauric acid with $CaCl_2$.

Formulation 10: Encapsulated tea tree and Novaluron with non-encapsulated pyrethrum and sesame oil and Novaluron.

Formulation 11: Tea tree oil encapsulated in Lauric acid by $CaCl_2$ with non-encapsulated Pyrethrum and Sesame oil.

Formulation 12: Tea tree oil encapsulated in Lauric acid by $CaCl_2$ with non-encapsulated Pyrethrum and Sesame oil.

Formulation 13: Citronella oil encapsulated in stearic acid by $CaCl_2$ with non-encapsulated Pyrethrum and Sesame oil.

Formulation 14: Tea tree oil encapsulated in stearic acid by $CaCl_2$ with free Pyrethrum and Sesame oil.

Formulation 15: Citronella oil encapsulated in decanoic acid by $CaCl_2$ with non-encapsulated Pyrethrum and Sesame oil.

Formulation 16: Tea tree oil encapsulated in decanoic acid by $CaCl_2$ with non-encapsulated Pyrethrum and Sesame oil.

Formulation 17: Citronella oil encapsulated in decanoic acid by $MgCl_2$ with free Pyrethrum and Sesame oil.

Formulation 18: Tea tree oil encapsulated in decanoic acid by $MgCl_2$ with free Pyrethrum and Sesame oil.

Formulation 19: Each of the above formulations was also encapsulated using fatty acids with divalent Ca or Mg salts, such as $Ca(OH)_2$ or $Mg(OH)_2$ or with a variety of other divalent or trivalent ions with varying counter ions.

B) Repellency Tests

Example 1

A cocktail of three essential oils of active ingredients such as citronella, lavender and geranium in a ratio of 1:1:1 dissolved in almond oil to form a 24% solution of active ingredients may be prepared in lab or purchased as a solution under the trade name Di-Tush™ (Tamar LTD, Israel).

In this example, 153 g of Di-Tush™ with an active essential oil concentration of 24% was mixed with 19.8 g of TDI and dispersed in an aqueous solution of 270 g water, and 2.7 g PVA. About 5 minutes after the microcapsules were formed 32.3 g of PEG 4000 dissolved in 75 g of water were added and the mixing was continued. At the end of the preparation 2.4 g Nefocide, 0.7 g Rodopol and enough Sodium biphosphate to bring the pH level to about 6 were added.

Formulation 1 with a 48% active concentration was also prepared in a similar fashion. Both formulations showed good mosquito repellent properties when sprayed on floors and wall. Both formulations showed a longer duration of activity than the non-encapsulated formulations.

Example 2

A solution of 35 g TDI mixed into 250 g of Formulation 1 having 6% active ingredient was added into 500 g water containing 5 g PVA using a high sheer mixer. To this were added 120 ml of water with 55.6 g PEG 4000. The mixing was continued for two hours at room temperature. To this dispersant were added 12 g Guar gum and 4 g of a fungicide (Nefocide). To break up the hydrogel, 10 g SDS (1%) was added.

When sprayed over half an acre area at a concentration of 50 ml to 1,000 ml of a 0.05 to 1% or at a 0.1% to 0.5% concentration over 1 acre of land in a neighborhood of residential homes it kept that area free of mosquitoes for 2 weeks while the neighboring areas were heavily infested. This formulation showed a longer duration of activity than the non-encapsulated formulations of the same essential oils or commercial non-encapsulated essential oils.

Example 3

100 g Citronella oil with 12 g decanoic acid dissolved therein were added to a rapidly stirring (high speed shear stirrer) solution of 250 ml $H_2O$ with 2.5 g PVA. To this, a solution of 22.8 g hexahydrate $MgCl_2$ in 20 ml $H_2O$ were added and stirred for two hours. Next, 20 g Pyrethrum, 2 g Sesame oil, 1.5 g methyl paraben, 8 ml Latron B 1956 and 3 g Guar gum were added with continual stirring for another 2 hours.

Example 4

Example 3 was repeated but without the Pyrethrum. Both Formulations 3 and 4 showed good mosquito repellant properties when sprayed on surfaces such as home and office walls, floors, ceilings, furniture, nets, screens, lawns, clothing, car seats, surfaces in animal husbandries, and aquacultures.

Example 5

Formulation 5 was prepared similarly to Formulation 1 using 93 g citronella oil, 10 g Pyrethrum and 1 g sesame oil instead of the Di-Tush product.

Example 6

Formulation 6 was prepared similarly to Formulation 1 using geranium oil as the encapsulated volatile essential oil instead of the Di-Tush product.

Example 7

Formulation 7 was prepared similarly to Formulation 1 using tea tree oil as the encapsulated volatile essential oil instead of the Di-Tush product.

Example 8

Formulation 8 was prepared similarly to Formulation 1 using lavender oil or clove oil as the encapsulated volatile essential oils instead of the Di-Tush product.

Example 9

Formulation 9 was prepared using the following ingredients and quantities in a process essentially identical to that disclosed for Formulation 1. Instead of the Di-Tush product, the following ingredients were used: 2.1 g PVA, 88 g ginger oil, 22 g cottonseed oil, 15.3 g TDI, 24.4 g PEG 4000, 1.8 g Nefocide and 0.5 g Rodopol.

Example 10

A formulation was prepared as a repellent against the common house fly (*Musca Domestica*).

250 grams of Di-Tush with an active essential oil concentration of 96% was mixed with 35 g of TDI and was dispersed in an aqueous solution of 500 ml water, with 5.0 g PVA. About 5 minutes after the microcapsules were formed 55.6 g of PEG 4000 dissolved in 120 ml of water was added and the dispersion continued until a uniform solution was formed (about 30 minutes to 2 hours). At the end of the preparation 4.0 g Nefocide and 10 g SDS (sodium dodecyl sulfate) were added. As stirring was continued, 12 grams Guar gum was added with the stirring being continued to achieve a uniform solution.

To determine the repellency of this formulation, about 400 laboratory-grown adult flies were used in every replica of the test. The flies were confined to a closed environment and the number of landed flies was counted on the sprayed and unsprayed paper sheets of the prepared formulation.

As may be seen from Table 3 below for all replicas the number of flies that landed on the sprayed paper was much less than for the control. In addition, in replica 1 after 48 h about 35% mortality was observed. For replica 2 after 1 h about 65% mortality was observed and after 5 h about 91% mortality was observed. A mortality of the whole population was observed after 24 hours.

TABLE 3

The repellent effect against house flies (*Musca Domestica*) of the formulation of Example 10.

| | The number of landed flies on sprayed and unsprayed paper sheet | | | | | |
|---|---|---|---|---|---|---|
| | replica 1 | | replica 2 | | replica 3 | |
| Exposure (h) | formula | control | formula | control | formula | control |
| 0 h | 0 | 31 | 0 | 24 | 0 | 9 |
| 0 h:15 min | 0 | 36 | 1 | 14 | 0 | 27 |
| 0 h:30 min | 0 | 30 | 0 | 15 | 0 | 21 |
| 0 h:45 min | 1 | 42 | 1 | 9 | 0 | 24 |
| 1 h | 0 | 34 | 0 | 11 | 1 | 8 |
| 1 h:15 min | 0 | 40 | 0 | 9 | 0 | 6 |
| 1 h:30 min | 2 | 51 | 0 | 6 | 0 | 8 |
| 1 h:45 min | 3 | 43 | 0 | 3 | 0 | 8 |
| 2 h | 2 | 64 | 0 | 2 | 1 | 12 |
| 2 h:15 min | 1 | 50 | 0 | 2 | 0 | 9 |
| 2 h:30 min | 0 | 56 | 0 | 3 | 0 | 7 |
| 2 h:45 min | 1 | 78 | 0 | 2 | 0 | 5 |
| 3 h | 2 | 43 | 0 | 4 | 0 | 8 |
| 3 h:15 min | 5 | 64 | 0 | 1 | 1 | 9 |
| 3 h:30 min | 9 | 58 | 1 | 3 | 1 | 8 |
| 3 h:45 min | 6 | 72 | 1 | 1 | 2 | 9 |
| 4 h | 2 | 116 | 1 | 0 | 0 | 11 |
| 4 h:15 min | 4 | 96 | 1 | 1 | 0 | 10 |
| 4 h:30 min | 4 | 82 | 1 | 2 | 0 | 12 |
| 4 h:45 min | 9 | 115 | 2 | 2 | 0 | 6 |
| 5 h | 15 | 83 | 1 | 5 | 0 | 5 |
| 5 h:15 min | 13 | 70 | 0 | 2 | 1 | 5 |
| 5 h:30 min | 26 | 78 | 0 | 2 | 1 | 5 |
| 5 h:45 min | 16 | 69 | 0 | 2 | 0 | 3 |
| 6 h | 16 | 54 | 0 | 1 | 0 | 3 |
| 24 h | 17 | 68 | after 1 h, about 65% mortality after 5 h, about 91% mortality; after 24 h, 100% mortality | | after 5 h, about 87% mortality after 24 h, 100% mortality | |
| 24 h:15 min | 16 | 54 | | | | |
| 24 h:30 min | 13 | 51 | | | | |
| 24 h:45 min | 14 | 56 | | | | |
| 25 h | 8 | 44 | | | | |
| 25 h:15 min | 9 | 48 | | | | |
| 25 h:30 min | 8 | 36 | | | | |
| 25 h:45 min | 11 | 43 | | | | |
| 26 h | 17 | 54 | | | | |
| 26 h:15 min | 15 | 38 | | | | |
| 26 h:30 min | 15 | 41 | | | | |
| 26 h:45 min | 17 | 39 | | | | |
| 27 h | 8 | 34 | | | | |
| 27 h:15 min | 23 | 29 | | | | |
| 27 h:30 min | 20 | 44 | | | | |
| 27 h:45 min | 28 | 41 | | | | |
| 28 h | 39 | 38 | | | | |
| 28 h:15 min | 41 | 49 | | | | |
| 28 h:30 min | 54 | 52 | | | | |
| 28 h:45 min | 37 | 48 | | | | |
| 29 h | 36 | 46 | | | | |
| 29 h:15 min | 34 | 33 | | | | |
| 29 h:30 min | 41 | 35 | | | | |
| 29 h:45 min | 48 | 48 | | | | |
| 30 h | 39 | 41 | | | | |
| 48 h | 34 | 32 | | | | |
| 48 h:15 min | 40 | 36 | | | | |
| | after 48 h c. 35% mortality | | | | | |

Example 11

An insecticide formulation was prepared against ants (*Tapinoma simrothi*) and cockroaches (*Germanica Blatella*). The formulation of is a combination of formulations A and B prepared as follows:

Formulation A:

112.5 g of tea tree oil and 18.3 g pyrinex were mixed with 18.7 g TDI. This solution was dispersed in an aqueous solution of 250 ml water containing 2.5 g dissolved PVA (polyvinyl alcohol). To this, 65 ml water, with 4.2 g ethylene diamine and 3.7 g diethylene triamine was added and the dispersion continued. After additional stirring a uniform dispersion was obtained into which 1.7 g Nefocide and 6.0 grams guar gum were added and the stirring was continued. The solution was then neutralized to pH 7 with for an acid such as citric acid. Next, 5.15 g sesame oil and 51.5 g pyrethrum were added and stirring was continued until a uniform mixture was obtained again.

Formulation B:

112.5 g of tea tree oil and 18.3 g pyrinex were mixed with 17.5 g of TDI which were dispersed in an aqueous solution of 250 ml water with 2.5 g dissolved PVA (polyvinyl alcohol). To this, 70 ml water with 23.3 g PEG 3350 was added and the dispersion mixing continued, after additional stirring, to form a uniform dispersion. Then, 2.0 g Nefocide, 5.0 g SDS and 6.0 g guar gum were added and stirring was continued. Finally, 5.15 g sesame oil and 51.5 g pyrethrum were added and stirring was continued until a uniform mixture was obtained.

Formulations A and B were next mixed in a ratio of 40 g of A and 20 g of B. To test the efficacy of this formulation a confined space in which ants or cockroaches were placed was sprayed with the combination and the percent mortality was determined. The results are given in Table 4 below.

TABLE 4

The efficacy of the combined formulation against ants (*Tapinoma simrothi*) and cockroaches (*Germanica Blatella*)

| Cockroaches (male) | | | | Ants | | | |
|---|---|---|---|---|---|---|---|
| 0.50% | 1% | 2% | Control | 0.50% | 1% | 2% | |
| Time 0 | | | | | | | |
| 0 | 0 | 0 | 0 | 0 | 0 | 0 | 0 |
| 2 | 50 | 30 | 75 | 0 | 100 | 100 | 100 | 0 |

TABLE 4-continued

The efficacy of the combined formulation against ants (*Tapinoma simrothi*) and cockroaches (*Germanica Blatella*)

| | Cockroaches (male) | | | | Ants | | |
|---|---|---|---|---|---|---|---|
| | 0.50% | 1% | 2% | Control | 0.50% | 1% | 2% |
| 4 | 90 | 85 | 95 | 0 | | | |
| 24 | 100 | 100 | 100 | 0 | | | |
| After 21 days | | | | | | | |
| 0 | 0 | 0 | 0 | | 0 | 0 | 0 |
| 2 | 0 | 0 | 20 | | 45 | 60 | 95 |
| 4 | 10 | 0 | 35 | | 100 | 100 | 100 |
| 6 | 10 | 0 | 45 | | | | |
| 24 | 15 | 35 | 95 | | | | |
| After 1 month | | | | | | | |
| 0 | 0 | 0 | 0 | | 0 | 0 | 0 |
| 2 | 0 | 5 | 5 | | 0 | 5 | 65 |
| 4 | 0 | 15 | 15 | | 45 | 80 | 100 |
| 6 | | | | | | | |
| 24 | 15 | 20 | 80 | | | | |
| After 1.5 month | | | | | | | |
| 0 | 0 | 0 | 0 | | 0 | 0 | 0 |
| 2 | 0 | 0 | 0 | | 5 | 25 | 35 |
| 4 | 0 | 0 | 0 | | 30 | 85 | 100 |
| 6 | 0 | 0 | 0 | | 70 | 95 | |
| 24 | 10 | 20 | 85 | | | | |
| After 2 month | | | | | | | |
| 0 | 0 | 0 | 0 | | 0 | 0 | 0 |
| 2 | 0 | 0 | 0 | | 0 | 0 | 0 |
| 4 | 0 | 0 | 0 | | 20 | 50 | 65 |
| 6 | 0 | 0 | 0 | | 50 | 70 | 80 |
| 24 | | | | | | | |
| After 2.5 month | | | | | | | |
| 0 | 0 | 0 | 0 | | 0 | 0 | 0 |
| 2 | 0 | 0 | 0 | | 15 | 87 | 91 |
| 4 | 0 | 0 | 5 | | 90 | 100 | 100 |
| 6 | 0 | 0 | 5 | | 100 | | |
| 24 | 15 | 25 | 20 | | | | |
| After 3 month | | | | | | | |
| 0 | | | | | 0 | 0 | 0 |
| 2 | | | | | 5 | 15 | 70 |
| 4 | | | | | 35 | 75 | 100 |
| 6 | | | | | 80 | 100 | |
| 24 | | | | | | | |

Example 12

The formation of essential oil microcapsules employed in drip irrigation systems was achieved by both interfacial polymerization and the method of the invention.

17.5 g TDI were mixed into 125 g clove oil and then added into 250 g water containing 2.5 g PVA using high sheer mixer. To this, were added 70 ml of water with 27.8 g PEG 4000. The mixing was continued for two hours at room temperature to afford a dispersant. To this dispersant were added 0.4 g of a xanthane gum (rodopol) and 2 g of a fungicide (Nefocide). To break up the hydrogel character of this emulsion, 5 g SDS (sodium dodecyl sulfate, 1%) was added.

When this formulation was fed into the water input for either subsurface drip irrigation systems or above ground drip irrigation systems ground, it was found to control effectively both bacteria and fungal growth in the tubing and orifices of the system.

Example 13

When the encapsulated essential oil of Example 1 was formulated together with herbicidal agents chosen from 2,6 dichlorobenzonitrile (Dichlobenil) and sodium methyldithiocarbamate (Metam), diquat and Paraquat, root growth into the water orifices was also effectively controlled as well as bacteria and fungal growth.

Example 14

Example 12 was repeated using 125 g thyme oil instead of clove oil with the same good results in controlling effectively both bacteria and fungal growth in the tubing and orifices of the irrigation systems.

Example 15

Example 12 was repeated using an essential oil having both antimicrobial and herbicidal activity, such as pine oil, tea tree oil or *eucalyptus* oil. Formulations comprising, each one or a combination of these essential oils showed good results in controlling effectively both bacteria and fungal growth in the tubing and orifices of the irrigation systems.

In another aspect of the invention, the formulation may be incorporated into wrapping or containing materials such as those used to contain or hold articles of various materials, fruits or vegetables or any other body which may be attacked by such insects. The wrapping or containing materials may be designed such as to allow slow or controlled release of the essential oils from the wrapper or the container to the articles contained therein during storage or shipment. The wrapping or containing materials may for example be pouches, plastic or paper bags, nylon sheets, polyester sheets, paper wrapping, plastic or other sealed containers, paper or plastic materials for hand or machine wrappings of fruits and vegetables, and the like.

Fruits and vegetables are characterized by high water content. Minimal water content is needed for it to remain useable product. Thus, drying out of fruits and vegetables has two effects: (1) it reduces the weight of the product and hence its value and (2) changes the chemical concentrations nutrients in the fruit or vegetable, a result that can enhance spoilage and at a minimum its taste. In all cases this is a considerable economic loss either to the seller or customer. Thus, there arises the need for a formulation which may form a coating around the fruit or vegetable, thereby reducing water evaporation and loss of nutrients. Use of such formulation may have a significant effect in maintaining the fruit or vegetable shelf life and time to market place.

Additionally, it is known that post-harvested fruits and vegetables are labile to attack by such microorganisms and insects which penetrate their skin for a variety of reasons. The formulations employed in this aspect of the invention were found useful in protecting post-harvested fruits and vegetables from such attacks by forming thereon a barrier which is capable of repelling the microorganisms and insects.

Thus, there is provided a film forming formulation which is capable of forming a coating on post-harvest fruits and vegetables. Both the film formed upon application and the essential oil contained within the microcapsules, or each of them independently prevent and control the attack by microorganisms and insects by first providing a physical shield and second by providing a long-term insecticidal or antimicroorganism protection.

After application, the fruits and vegetables that have been covered by the formulation are allowed to dry, thereby allowing the physical barrier and prophylactic shield to form.

The formulations used with this application comprise encapsulated essential oils which may be carried in an aqueous medium with other agents such as polymers and surfactants, present therein in order to stabilize the suspension.

In one preferred embodiment, the formulation further comprises coating agents, which may or may not be identical to the polymers which stabilize the suspension, and which may form a protected coating on the sprayed substrate, i.e. fruit or vegetable.

Example 16

A solution of 35 g TDI mixed into 250 g of tea tree oil was added into 500 g water containing 5 g PVA using a high sheer mixer. To this is added 120 ml of water with 55.6 g PEG 4000. The mixing was continued for two hours at room temperature. To this dispersant were added 12 g Guar gum and 4 g of a fungicide (Nefocide). To break up the hydrogel character of this emulsion, 10 g SDS (sodium dodecyl sulfate, 1%) was added.

This formulation herein labeled N262 was tested on onions, carrots and potatoes against control (untreated) and others commercial formulations by the names HPP, Oxyfor, Shemer in two parameters: Lost of Weight and Rotting, as detailed in Tables 5 and 6 below.

3. Commercial wash group—carrots dipped in a solution of 150 ppm chlorine+0.2% iprodione (labeled Com);

4. Treated group II—carrots having been treated as in group 2, and thereafter with the commercial wash as with group 3 (labeled Com+T);

5. N262 group—carrots dipped in a 2% solution of N262 (labeled EO1);

6. Treated group III— carrots treated as in group 2, and thereafter dipped in a 2% solution of N262 (labeled EO1+T);

7. N262 group II— carrots dipped in a 4% solution of N262 (labeled EO2);

8. Treated group IV— carrots treated as in group 2 and thereafter dipped in a 4% solution of N262 (labeled EO2+T);

9. N262 group III— carrots dipped in a 6.6% solution of N262 (labeled EO3); and

10. Treated group V— carrots treated as in group 2 and thereafter dipped in a 6.6% solution of N262 (labeled EO3+T).

The results are shown in Table 7 below. It may be concluded that formulation N262 at a concentration of 2% reduces the inoculation of carrots more than the other treatments and may be used as a replacement of commercial wash (if the goal is to replace the chemicals by friendly materials).

TABLE 5

Post harvest Red and Brown Onions "Lost of Weight" Tests (%)

| Red Onion | | | | | Brown Onion | | | |
| --- | --- | --- | --- | --- | --- | --- | --- | --- |
| 4 months | 3 months | 2 months | 1 month | Treatment | 4 months | 3 months | 2 months | 1 month |
| 24.6 | 9.1 | 4.5 | 3.2 | Control | 16.9 | 12.5 | 5.8 | 3.3 |
| 15.6 | 9.3 | 6.3 | 4.5 | HPP | 9.4 | 7.2 | 4.3 | 3.1 |
| 22.8 | 12.3 | 5.5 | 2.8 | Oxyfor | 20.6 | 9.3 | 4.1 | 2.7 |
| 30.7 | 15.5 | 6.5 | 3.5 | Shemer | 13.3 | 8.8 | 4.3 | 2.7 |
| 16.5 | 8.6 | 4.2 | 2.3 | N262 | 11.5 | 8.1 | 5 | 3.6 |

TABLE 6

Post harvest Red and Brown Onions "Rotting" Tests (%)

| Red Onion | | Brown Onion |
| --- | --- | --- |
| 4 month | Treatment | 4 months |
| 22 | Control | 20 |
| 19.7 | HPP | 10.3 |
| 21.1 | Oxyfor | 13.7 |
| 27.1 | Shemer | 10 |
| 12.1 | N262 | 12.3 |

Additional experiments were carried out to determine the effect of formulation N262 on the decaying of stored carrots. The experiment was conducted with carrots grown in Kibbutz Alumim. The carrots were dipped in the different solutions for 30 seconds, stored for 1 month in a storage room at a temperature of 0-1 C.° and for a further 6-day shelf life period at 25 C.°.

The treatment of carrots followed the next procedure: Several groups of carrots were used:

1. Control group—untreated carrots (labeled C);

2. Treated group—carrots dipped in a suspension of pathogens: *Sclerotinia sclerotiorum, Alternaria* alternate, *A. radicina* (labeled T);

TABLE 7

Results of N262 on both fungal and bacterial decay of carrots exposed pathogens *Sclerotinia sclerotiorum, Alternaria alternate, and A. radicina*.

| Decay-total (%) | Decay-mix (%) | Decay caused by bacteria (%) | Decay caused by fungi (%) | Treatments |
| --- | --- | --- | --- | --- |
| 4.5 | 1.4 | 3.1 | 0 | C |
| 57 | 0 | 0 | 57 | T |
| 2.4 | 2.4 | 0 | 0 | Com |
| 11.9 | 2.8 | 0.3 | 8.8 | Com + T |
| 2.65 | 0.7 | 2.0 | 0 | EO1 |
| 21.3 | 2.3 | 19 | 0 | EO1 + T |
| 9.6 | 5.8 | 3.8 | 0 | EO2 |
| 31.2 | 1.0 | 4.2 | 26 | EO2 + T |
| 3.3 | 2.0 | 1.3 | 0 | EO3 |
| 72.3 | 0.3 | 0 | 72 | EO3 + T |

Additional experiments were carried out to determine the effect of formulation N262 on the decaying of stored sweet potatoes against Resopous and other rotting. The experiment was done with sweet potatoes by Agronomia Agriculture Company. The sweet potatoes were dipped in the different solutions for few seconds, and stored one month in a storage room at a temperature of 0-4 C.°.

The treatment of sweet potatoes followed the next procedure: Several groups of carrots were used:

1. Control group—untreated sweet potatoes (labeled C);
2. Treated group—sweet potatoes dipped in water (labeled W);
3. Treated group I—sweet potatoes having been treated by 0.5% of BotanoCap formulation called B262 as in group 2 (labeled B1); and
4. Treated group II—sweet potatoes having been treated by 3.0% of BotanoCap formulation called B262 as in group 2 (labeled B2); and thereafter with the commercial formulation by the name of Magnet (Imazalil) as with groups 3 and 4 (labeled M).

The results are shown in Table 8 below. It may be concluded that formulation B262 at a concentration of 0.5% and 3% reduces the inoculation of sweet potatoes more than the other treatments and may be used as a replacement to commercial wash against Resopous, especially if the goal is to replace the chemicals by friendly materials.

TABLE 8

Results of B262 on both Resopous and other causes decay of sweet potatoes in storage room.

| Rotting by Resopous and other causes after one month (%) | Treatments |
|---|---|
| 16.48 | C |
| 17.45 | W |
| 10.98 | B1 |
| 12.33 | B2 |
| 20.81 | M |

Post Harvest Solid Formulations

Example 17

A solid core formulation containing 64% tea tree was prepared as follows:
First, the following solutions and components were prepared:
A) 70 grams Aerosil A 300 were weighed.
B) 22.8 grams of toluene diisocyanate (TDI) were weighed and dissolved into 181.2 grams of tea tree oil.
C) A solution was prepared by mixing 5.4 grams of ethane diamine (EDA) and 4.7 grams of diethylene triamine (DETA) in 10.6 grams water.

Preparation of Final Formulation:
70 grams Aerosil A 200 were placed in a rotating multiplex production drum (6005/mum Multiplex—Apex Construction LTD London). The TDI dissolved in the tea tree oil was added thereto and this solution was uniformly absorbed into the Aerosil A 300 powder. The tea tree/TDI solution was added in one step into the drum and the drum was rotated for 60 minutes to obtain a uniform distribution of powder. The aqueous solution of EDA/DETA was then sprayed into the drum, which was rotated for additional 2 hours.

The above formulation, when checked for antibacterial and antifungal activity, gave excellent results and when applied as a powder on the carrots or within the container of post harvest carrots prevented bacterial and fungal infestations as compared to the control.

The same reaction was repeated, substituting the TDI of Fluka with Voronate 220.

The microcapsule powder was also formulated in an aqueous carrier and applied to the carrots with equally good results.

Example 18

Example 17 was repeated using Oregano oil instead of tea tree oil to give a solid particle formulation containing 64% oregano. This formulation, when checked for antibacterial and antifungal activity, gave excellent results and when used on post harvest potatoes and prevented bacterial and fungal infestations as compared to the control.

Example 19

Example 17 was repeated using a mixture of tea tree and oregano oil (in a ratio of 1:1) to give a solid particle formulation having 32% tea tree and 32% oregano. This formulation, when checked for antibacterial and antifungal activity, gave excellent results and when used on post harvest potatoes prevented bacterial and fungal infestations as compared to the control.

Example 20

Decanoic acid (12 grams) was dissolved in tea tree oil (100 grams) and this solution was added to a rotating drum containing 70 grams Aerosil A 200, and rotated for 60 minutes at a speed that gives a uniform distribution. After this time, a solution containing 3.5 grams NaOH and 7 grams CaCl$_2$ in 100 ml of water, was sprayed into the rotating drum and rotated for an additional two hours. The final microcapsules were found to have good antibacterial activity.

Food Additives for Human and Animal Consumption
Background—

The food industry makes use of unsaturated fatty acids in a variety of products suitable for the consumption of animals such as mice, rats, cows or cattle, horses, sheep, goats, and primates, including apes, chimpanzees, orangutans, fish, shellfish, crustaceans, birds (e.g., chickens, roosters, etc.), humans or domesticated animals (e.g., dogs and cats). Such fatty acids could for example, be eicosapentaneoic acid (EPA), docosahexaenoic acid (DHA), aracadonoic acid (ARA), and conjugated linoleic acid and linolenic acid (CLA). These unsaturated fatty acids exhibit characteristics which may affect their processing, manufacturing, storage, odor, compatibility and oxidation.

Encapsulation of these fatty acids may solve some of these problems and make them suitable for direct consumption or incorporation in food products. Other food ingredients, such as vitamins, nutritional supplements, minerals, herbal products, food additives, amino acids, and the like, including, for example, beta-carotene, lutein, zeazanthin, iron salts, copper salts, selenium salts, flavonoids, co-enzyme Q10, herbs, spices, flavorants and extracts (such as allicin or garlic extract), are also candidates for encapsulation.

Summary—

The encapsulated essential oil formulations employed are based on the encapsulating membranes and essential oils which are GRASS and/or FDA approved. In fact, all agents contained in the microcapsules or the formulations comprising them, are non-toxic to both humans and animals. Such formulations have been prepared using fatty acids or alkanoic acids as disclosed hereinabove. In brief, the acids are dissolved in the essential oil, and then emulsified in an aqueous solution. The acids are next crosslinked by multivalent cations such as Ca or Mg or Fe or other multivalent cations dissolved within the aqueous solution.

More specifically, this method comprising:

(a) admixing at least one alkanoic acid with at least one essential oil;

(b) admixing the mixture of step (a) with an aqueous basic solution to obtain a suspension; and (c) admixing into the suspension of step (b) an aqueous salt solution comprising at least one multivalent cation, thereby obtaining an aqueous suspension of microcapsules of microencapsulated essential oil.

In one embodiment, the method further comprises the step of filtering and collecting the wax or solid particles.

In another embodiment, the particles are not separated from the liquid carrier and the formulation is used as is.

When separating the solid microcapsules from the aqueous media, small amounts of essential oils may remain unencapsulated. In order to obtain oil-dry microcapsules, an absorbent capable of absorbing the excess oil is added, typically in small amounts. The absorbent may be selected amongst, for example, Celluloses, starch powders or Aerosil™ silicas such Aerosil™ 200 or 300, commercially available from Degussa. In some applications the Aerosil™ is the preferred absorbent.

The invention further provides a method for preparing a microcapsule formulation containing a plurality of edible microcapsules, each having a core containing at least one essential oil and an outer shell surrounding said core, said method comprising:

(a) admixing at least one alkanoic acid with at least one essential oil;

(b) admixing the mixture of step (a) with an aqueous basic solution to obtain a suspension; and (c) admixing into the suspension of step (b) an aqueous salt solution comprising at least one multivalent cation, thereby obtaining an aqueous suspension of microcapsules of microencapsulated essential oil.

In one embodiment, the core containing at least one essential oil further comprises at least one additive, said additive being preferably a food enhancing additive.

In another embodiment of the invention, additives are added to the formulation before step (c). The additive may be in a solid form or a liquid form or a suspension of two or more such agents. Such additives may be selected from active pharmaceutical agents, natural or synthetic antioxidants, food supplements, vitamins, colorants, odorants, oils, fats, flavors, nonvolatile natural essential oils or other dispersants or emulsifiers. In some specific embodiments, the additives may be selected from gamma-linolenic acids, citrus oils such as orange oils, nutritional supplements such as Vitamin A, Vitamin E, Vitamin C, and Vitamin D, tocopherols, tocotrienols, phytosterols, Vitamin K, beta-carotene, marine oils, and omega-3 fatty acids, $CoQ_{10}$, lipid soluble derivatives of more polar antioxidants, e.g. ascobyl fatty acid esters, plant extracts (e.g., rosemary, sage and oregano oils), algal extracts, and synthetic antioxidants (e.g., BHT, TBHQ, ethoxyquin, alkyl gallates, hydroquinones, tocotrienols).

Specific examples of oils which may be added include, but are not limited to, animal oils (e.g., fish oil, marine mammal oil, etc.), vegetable oils (e.g., canola or rapeseed), mineral oils, derivatives thereof or mixtures thereof.

The additive may be a purified or partially purified oily substance such as a fatty acid, a triglyceride or ester thereof, or a mixture thereof.

In another embodiment, the additive is at least one carotenoid (e.g., lycopene), a satiety agent, a flavor compound, a drug (e.g., a water insoluble drug), a particulate, an agricultural chemical (e.g., herbicides, insecticides, fertilizers), or an aquaculture ingredient (e.g., feed, pigment).

Specific examples of suitable fish oils include, but are not limited to, Atlantic fish oils, Pacific fish oils, Mediterranean fish oils, light pressed fish oil, alkaline treated fish oil, heat treated fish oil, light and heavy brown fish oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmonids oil, shark oil, and the like.

Once the oil or water immiscible liquid is converted into a solid or wax type particle it may be filtered to recover the solids in the suspension or the suspension may be used as is.

When there is a need to preserve the encapsulated oils prior to use, formulation adjuvants may be added to the formulation. These improve suspension stability and the ease of application. Such formulation adjuvants may be selected from but are not limited to density balancing agents, surfactants, thickeners, biocides, dispersants, antifreeze agents, salts and any combination thereof. The formulation adjuvants may be added to the encapsulated oils at a concentration of about 0.01% to about 30% by weight of the encapsulated oil product.

The method of the invention may be used for the conversion of liquids to free-flowing powders or compressed solids, which can be used as components in the manufacturing of a final product, to store a substance, to separate reactive substances, to reduce toxicity of a substance, to protect a substance against oxidation, to deliver a substance to a specified environment and/or to control the rate of release of a substance.

In another preferred embodiment of the invention, the encapsulated solid particles can be used for delivering any of the loaded substances described herein to a subject, which may include mammals such as mice, rats, cows or cattle, horses, sheep, goats, and primates, including apes, chimpanzees, orangutans, fish, shellfish, crustaceans, birds (e.g., chickens, roosters, etc.), humans or domesticated animals (e.g., dogs and cats).

As disclosed hereinabove, the alkanoic acids employed in the method of the invention are preferably selected amongst those having melting point temperatures higher than 25° C. Additionally, the alkanoic acids are preferably 10 to 45 carbon in length.

Examples of such acids which are suitable for this application are unsaturated acids selected from but not limited to 11-octadecenoic acid or 5,8,11,14-eicosatetraenoic acid, and omega-3 fatty acid. Examples of omega-3 fatty acids include, but are not limited to, α-linolenic acid (18:3-omega-3), octadecatetraenoic acid (18:4-omega-3), eicosapentaenoic acid (20:5-omega-3) (EPA), docosahexaenoic acid (22:6-omega-3) (DHA), docosapentaenoic acid (22:5-omega-3) (DPA), eicosatetraenoic acid (20:4-omega-3), uncosapentaenoic acid (21:5-omega-3), docosapentaenoic acid (22:5-omega-3) including any derivatives thereof and any combinations thereof.

Possible derivatives of omega-3 fatty acids may include esters derivatives, branched or unbranched $C_1$-$C_{30}$ alkyl esters, branched or unbranched $C_2$-$C_{30}$ alkenyl esters, or branched or unbranched $C_3$-$C_{30}$ cycloalkyl esters such as phytosterol esters and C1-C6 alkyl esters.

The fatty acids may be extracted from natural sources including, however not limited to, aquatic organisms (e.g., anchovies, capelin, Atlantic cod, Atlantic herring, Atlantic mackerel, Atlantic menhaden, salmonids, sardines, shark, tuna, etc) and plants (e.g., flax, vegetables, etc) and microorganisms (e.g., fungi and algae).

The concentration of oils within a formulation may vary between 0.01 to 90% and preferably 60% or higher for applications needed to convert oils to solids or in the range of 25% for aqueous formulations such as encapsulated pyrethrum.

In a preferred embodiment of the invention, the resultant encapsulated materials suitable for animal consumption are in the form of a dry, free-flowing powder. These materials have the advantage of achieving and maintaining consistently high active agent levels, and/or excellent oxidation resistance. The encapsulated material prepared with the present encapsulating agents consistently achieves and maintain a relatively high level of the active agent. The active agent may be present in an amount of from about 5 to 90% (wt/wt) based upon the encapsulated material. In another embodiment, the active agent is present in an amount ranging from about 15 to 60% (w/w). A high level of active agent is desirable to reduce the cost of producing the final product as encapsulating agents are often expensive. Further, some encapsulating agents may contribute adverse or undesirable properties to the final system and it is thus desirable to reduce the amount of encapsulating agent used.

The introduction of certain agents in their encapsulated form also provides the means to overcome problems associated with insolubility or low solubility of the agent in the media. Thus, encapsulating the food additive, e.g., vitamins, affords a form of the additive which may be dissolved or dispersed into the foodstuff at a concentration which is homogenous and measurable.

It is important not only to achieve a high level of active agent, but also to maintain it so as to enable a longer shelf life. To further increase oxidation resistance, an anti-oxidant and/or reducing agent may be added to the oil. The encapsulated material is stable when stored as a powder and releases the active agent upon exposure to moisture. The resultant encapsulated material may be used at any level desired, the amount being dependent upon the amount of active agent to be incorporated and the product in which it is to be used.

In one embodiment in which the encapsulated materials are used in a food product, the encapsulated material is used in an amount of from about 0.01 to about 10% by weight of the food product and in another embodiment up to about 5% (w/w).

The solid encapsulated particles of the invention may be used in foodstuffs. The term "foodstuff" as used herein refers to any article that can be consumed (e.g., eaten, drank, or ingested) by a subject human, animal or fish.

In one embodiment, the solid encapsulated particles of the invention may be used as nutritional supplements to a foodstuff. In another embodiment of the invention, the foodstuff could be a baked good, a pasta, a meat product, a frozen dairy product, a milk product, a cheese product, an egg product, a condiment, a soup mix, a snack food, a nut product, a plant protein product, a hard candy, a soft candy, a poultry product, a processed fruit juice, a granulated sugar (e.g., white or brown), a sauce, a gravy, a syrup, a nutritional bar, a beverage, a dry beverage powder, a jam or jelly, a fish product, or pet companion food. In another aspect, the foodstuff is bread, tortillas, cereal, sausage, chicken, ice cream, yogurt, milk, salad dressing, rice bran, fruit juice, a dry beverage powder, rolls, cookies, crackers, fruit pies, or cakes.

In another embodiment the solid encapsulated particles of the invention may be used in pharmaceutical formulations. Pharmaceutical formulations may also include additional carriers, as well as thickeners, diluents, buffers, preservatives, surface-active agents and other components. Pharmaceutical formulations may also include one or more additional active ingredients which may or may not be by themselves active pharmaceuticals such as antimicrobial agents, anti inflammatory agents, anesthetics, and the like.

In a further embodiment of the invention, the solid encapsulated particles prepared by any one of the methods disclosed herein may be used in personal care products including antiperspirants, deodorants, soaps, fragrances, and cosmetics; hair care products, such as hair sprays, mousses, shampoos, cream rinses, and gels; paper products such as diapers, sanitary napkins, paper towels, tissues, toilet tissues; animal care products such as kitty litter; and household products such as carpet cleaners, and air fresheners.

The fatty acid (e.g., decanoic, or stearic or palmitic carboxylic acids) added to the oil may act as a surfactant to form the dispersion of the oil in the aqueous medium. However ionic or non-ionic surfactant may be needed. Such surfactant may be added during manufacture of the microcapsules in order to facilitate or control the size of the microcapsules and/or may be added after the microcapsules are manufactured in order to break up a gel that results from the microencapsulation and afford a flowable non-gel formulation. One preferred surfactant is sodium dodecyl sulfate (SDS). It may preferably be added in concentrations of 0.1 to 10% and most preferably in concentrations of 0.5% to 5%.

Other non-limiting examples of preferred additives in addition to surfactants are stearic barrier polymers, which help maintain particle separation, such as polyvinylpyrrolidone (PVP), polyvinyl alcohol (PVA) and poly(ethoxy) nonylphenol. In some cases it is desirable to adjust the pH of the finished microcapsule formulation as, for example, when the solution of finished microcapsule is combined with other pesticides. Conventional reagents for adjustment of acidity or alkalinity may be used, including for example, hydrochloric acid, citric acid, sodium hydroxide, sodium carbonate, and sodium bicarbonate. Additional stabilizes that may be added are alginates, Xanthan gums, carboxymethyl cellulose, sodium salt, Xanthan gum, Karya gum and Locust bean gum, and the like.

PVP is available at various molecular weights in the range of from about 20,000 to about 90,000 and all these can be used, but PVP of about 40,000 MW is preferred. Poly(ethoxy)nonylphenol are available under the trade-mark Igepal, with various molecular weights depending on the length of the ethoxy chain. Poly(ethoxy)nonylphenol can be used but Igepal 630, indicating a molecular weight of about 630, is the preferred poly(ethoxy)nonylphenol. Other examples of surfactants include polyether block copolymers, such as Pluronic and Tetronic, polyoxyethylene adducts of fatty alcohols, such as Brij surfactants and esters of fatty acids, such as stearates, oleates, and the like. Examples of such fatty acids include sorbitan monostearate, sorbitan monooleate, sorbitan sesquioleate, and the like. Examples of the alcohol portions of the fatty esters include glycerol, glucosyl and the like. Fatty esters are commercially available as Arlacel C.R surfactants. Surfactants vary in their surfactant properties, and the surfactant properties affect the size of the microcapsules formed. Other things being equal, use of PVP of 40,000 MW will give larger microcapsules than Igepal 630. The surfactant used, and also the degree and extent of agitation, affect the size of the microcapsules obtained. In general, they may be from about 1 to about 100 micron in size, depending upon the conditions used. Other surfactants to form dispersions and emulsifiers may also be used such as sodium, potassium, magnesium, and calcium or ammonium salts of lignin sulfonate.

As stated hereinbefore, the encapsulated solid particles may be either recovered from the reaction mixture or re-suspended in said non-volatile vehicle or in a solution containing thereof. Alternatively, any medium, aqueous or otherwise, which comprises the microcapsules, may be treated without initial separation from the medium in which they are manufactured (water) with at least one non-volatile vehicle. In most cases said medium is water. In cases where separation is preferred, the collection of the microcapsules may be achieved, depending on their size, by centrifugation or filtration and washed with several portions of an appropriate solvent, e.g. distilled water, to remove free reactants from the surface.

Additionally, these particles may be dispersed or suspended in said non-volatile liquid or solid vehicle. In some cases, said non-volatile vehicle is a particulate solid, e.g. powder, by which the dispersion is preferably done by admixing an effective amount of dry microcapsules with said vehicle. In some cases, said non-volatile vehicle is a liquid, by which the suspension is preferably prepared by mechanically stirring an effective amount of the microcapsules in said vehicle.

There is, thus, also provided a method for preparing edible microcapsules, said method comprising:

(a) admixing at least one alkanoic acid with at least one essential oil;

(b) admixing the mixture of step (a) with an aqueous basic solution to obtain a suspension;

(c) admixing into the suspension of step (b) an aqueous salt solution comprising at least one multivalent cation, and (d) collecting the microcapsules from the aqueous media, thereby obtaining microcapsules of at least one microencapsulated essential oil.

These microcapsules may be added to food products (such as sausages, salamis and processed meats in general, cheeses of all types, etc) to prevent or delay spoilage or discoloration caused by microorganisms. The encapsulated essential oil formulations may also include food preservative agents including, but not limited to benzoic acid, sodium benzoate, and calcium propionate, methyl paraben, ethyl paraben, propyl paraben or butyl paraben.

The preservative or food additive microcapsules may comprise between 0.01 to 5% or preferably 0.1% and 1% of essential oil and 0.1% benzoic acid or paraben. The ingredients may be added to the foodstuff separately or together as may be necessary. The encapsulated essential oil may be added at a level in which there is no affect on taste or smell, or it may be added at higher levels if the smell or taste of an essential oil is desired. In some cases the encapsulated essential oil additive or preservative is used such that the concentration of oil, derivative or active ingredient thereof is between 0.01% and 1% and the concentration of benzoic acid or paraben is from 0.01% to 1%.

In one embodiment of the invention, the formulation comprises oil of fennel and methyl paraben wherein the oil of fennel is used at a concentration of 0.2% and the methyl paraben are used at a concentration of 0.1%.

The essential oil formulation used as a food preservative may be effective against inhibiting many microorganisms such as, and without being limited thereto: *Listeria monocytogenes*; *Salmonella enteriditis*; *Staphylococcus aureus* and vancomycin-resistant *Enterococcus*.

The essential oils may be chosen from those with antimicrobial and/or fungicidal properties as disclosed hereinbefore in reference to other applications. Examples of such oils which may be used are Tea tree oil, thyme oil, Clove oil, *Eucalyptus* oil and oregano oil, citronella oil, basil oil, oil of fennel and oil of anise. Thus, the microcapsules may be used as preservatives and disinfectants for the storage of fruits, vegetables and grains in confined spaces such as cargo ships, silos storage houses, barns, silos. When used in these applications it may be applied as a powder it may be distributed to the surfaces of container or confined area or it may be packaged in porous bags or bottles and placed strategically in containers or confined areas containing fruits, vegetables and grains for the purpose of disinfection and preservatives against microbial or fungal growth for example or insect infestation.

Example 1

Decanoic acid (12 gr) was dissolved in tea tree oil (100 gr). The resulting solution was added to a rapidly stirring (high speed shear stirrer) solution of $H_2O$ 250 ml with PVA (2.5 gr). To this, hexahydrate $MgCl_2$ (22.8 gr) dissolved in $H_2O$ (20 ml) was added and the solution was stirred for two hours, after which Guar gum (3 gr) was added with continual stirring for another 2 hours.

When this formulation was added to sausages it prevented bacterial and fungal growth.

Example 2

Example 1 was repeated, replacing the tea tree oil with 125 g clove oil. The resulting solution was added to both white and yellow cheese during their manufacture controlling effectively both bacteria and fungal growth.

Example 3

Encapsulation of powder of cod liver oil was achieved as follows:

Solution A was prepared by dissolving 25 gr. of Stearic acid in 75 gr. of Cod liver oil at 70-80° C.

Solution B was prepared by adding a solution of 3.5 gr. NaOH in 30 ml of water to solution A while stirring for 10 min.

Solution C was prepared by adding a solution of 7 gr. $CaCl_2.2H_2O$ in 70 ml of water to a mixture of solutions A+B while stirring for 10 min.

The reaction mixture was filtered through Buchner funnel and air-dried. 10 gr of the dried product was next mixed with 2.5 gr Aerosil 200 or 300 to absorb residual non-encapsulated oil. The final product contained 60% cod liver oil as the active ingredient.

The encapsulated product had a fish odor. When the entire process of dissolution and encapsulation was carried out under a nitrogen atmosphere the product no longer had a fish odor.

Example 4

Encapsulation of oil used in the manufacture of animal feed was prepared as follows:

Solution A was prepared by dissolving 25 gr. of stearic acid in 75 gr of a vegetable oil at 60° C.

Solution B was prepared by adding a solution of 3.5 gr NaOH in 30 ml of water to solution A with stirring at 60° C.

Solution C was prepared by adding a solution of 7 gr $CaCl_2.2H_2O$ in 70 ml of water to a mixture of solutions A+B with stirring for 10 min at 60° C.

The reaction mixture was filtered through a Buchner funnel and air-dried at room temperature. 10 gr. of the dried material was mixed with 2.5 gr. Aerosil 200 or 300. The final product contained 60% of the vegetable oil as the active ingredient.

Example 5

The encapsulation of Pyrethrum in stearic acid/Ca salt was achieved as follows:

Solution A was prepared by dissolving 15 gr. of stearic acid in 50 gr. of pyrethrum at 60° C.

Solution B was prepared by adding a solution of 2.1 gr. of NaOH in 20 ml of water to solution A while stirring for 10 min.

Solution C was prepared by adding a solution of 4.2 gr. of $CaCl_2.2H_2O$ in 40 ml of water to a mixture of solutions A and B with stirring for 10 min.

Solution D was prepared by mixing a mixture of solutions A, B and C with a solution of 10 gr. SDS, 0.4 gr. of Irganox 1076, 0.4 gr. Tinuvin 770 and 850 ml of water. The reaction mixture was stirred with high sheer mixture for 30 min. The pH was adjusted to 7 using Citric acid. The reaction mixture was additionally stirred for 30 min, at which point 3.5 gr. Rodopol 24 was added with stirring for 30 min.

The invention claimed is:

1. A microcapsule comprising an encapsulating amphiphatic shell surrounding a core, said encapsulating amphiphatic shell comprising a multivalent salt form of at least one alkanoic acid, and said core comprising at least one essential oil or derivative thereof, which microcapsules contain the essential oil in an amount of 60-95% of the weight of the microcapsule.

2. The microcapsule of claim 1, wherein said essential oil is selected from the group consisting of anise oil, *angelica* oil, basil oil, bay oil, bergamot oil, bois de rose oil, camphor oil, *cananga* oil, cardamom oil, caraway oil, cedar oil, cedarwood oil, *Chamaecyparis obtusa* oil, chamomile oil, cinnamon oil, citronella oil, clove oil, copaiba balsam oil, cumin oil, clove oil, coriander oil, dill oil, *eucalyptus* oil, fennel oil, garlic oil, geranium oil, grapefruit oil, ginger oil, guaiac oil, hiba oil, iris oil, Japanese mint oil, jasmine oil, lavender oil, lemon oil, lemongrass oil, linaloe oil, *Lindera* oil, mandarin oil, mint oil, neroli oil, onion oil, orange oil, oregano oil, palmarosa sofia oil, patchouli oil, parsley oil, pepper oil, peppermint oil, *perilla* oil, Peru balsam oil, petitgrain oil, pine oil, pine needle oil, rose oil, rosemary oil, sandalwood oil, spearmint oil, star anis oil, sweet orange oil, tangerine oil, tea seed oil, tea tree oil, thyme oil, tolu balsam oil, tuberose oil, turmeric oil, vetivert oil, western mint oil, wintergreen oil and any combination thereof.

3. The microcapsule of claim 1, wherein said core further comprises one or more insect growth regulators (IGR).

4. The microencapsulated essential oil formulation of claim 3, wherein said insect growth regulator (IGR) is selected from the group consisting of pyriproxyphen, azadirachtin and novaluron.

5. The microcapsule of claim 1, wherein the weight of alkanoic acid is about 12% of the weight of the at least one essential oil in the microcapsule.

6. The microcapsule of claim 1, further comprising a nonvolatile oil.

7. The microcapsule of claim 6, wherein said non-volatile oil is selected from the group consisting of pyrethrum oil, sesame oil, cottonseed oil and combinations thereof.

8. A microencapsulated essential oil formulation comprising a plurality of the microcapsules of claim 1, wherein said formulation is solid or liquid.

9. The microencapsulated essential oil formulation of claim 8, wherein the formulation is homogenous or heterogeneous.

10. The microencapsulated essential oil formulation of claim 8, further comprising at least one absorbent is selected from the group consisting of celluloses, starch powders, fumed silicas and any combination thereof.

11. The microencapsulated essential oil formulation of claim 8, further comprising at least one ionic or non-ionic surfactant.

12. The microencapsulated essential oil formulation of claim 8, further comprising at least one additive selected from the group consisting of an active pharmaceutical agent, an antioxidant, a food supplement, an insect growth regulator (IGR), an insecticide, an acaracide, a fungicide, a nematicide, a vitamin, a colorant, an odorant, a flavor, a dispersant, a steric barrier polymer, an emulsifier and any combination thereof.

13. The microencapsulated essential oil formulation of claim 12, wherein said additive is encapsulated or unencapsulated.

14. The microencapsulated essential oil formulation of claim 12, wherein said additive is an insecticide or an insect growth regulator (IGR).

15. The microencapsulated essential oil formulation of claim 14, wherein said insecticide or said insect growth regulator (IGR) is selected from the group consisting of pyriproxyphen, azadirachtin and novaluron.

16. The microencapsulated essential oil formulation of claim 8, further comprising an encapsulated or unencapsulated non-volatile oil.

17. The microencapsulated essential oil formulation of claim 16, wherein said non-volatile oil is selected from the group consisting of pyrethrum oil, sesame oil, cottonseed oil and combinations thereof.

* * * * *